(12) United States Patent
Weimann

(10) Patent No.: US 10,821,084 B2
(45) Date of Patent: *Nov. 3, 2020

(54) DIHYDROMYRICETIN COMPOSITIONS

(71) Applicant: REMY BIOSCIENCES, INC., Irvine, CA (US)

(72) Inventor: Ludwig Weimann, San Diego, CA (US)

(73) Assignee: Remy Biosciences, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/262,152

(22) Filed: Jan. 30, 2019

(65) Prior Publication Data

US 2019/0231711 A1 Aug. 1, 2019

Related U.S. Application Data

(60) Provisional application No. 62/624,596, filed on Jan. 31, 2018.

(51) Int. Cl.
| | | |
|---|---|---|
| *A61K 9/70* | (2006.01) | |
| *A61K 31/05* | (2006.01) | |
| *A61K 31/125* | (2006.01) | |
| *A61K 31/352* | (2006.01) | |
| *A61K 36/71* | (2006.01) | |
| *A61K 31/4045* | (2006.01) | |
| *A61K 47/32* | (2006.01) | |
| *A61P 43/00* | (2006.01) | |
| *A61P 5/24* | (2006.01) | |
| *A61P 25/32* | (2006.01) | |
| *A61F 13/02* | (2006.01) | |
| *A61M 35/00* | (2006.01) | |
| *A61K 9/00* | (2006.01) | |

(52) U.S. Cl.
CPC ........ *A61K 9/7084* (2013.01); *A61F 13/0276* (2013.01); *A61K 9/006* (2013.01); *A61K 9/703* (2013.01); *A61K 9/7053* (2013.01); *A61K 31/05* (2013.01); *A61K 31/125* (2013.01); *A61K 31/352* (2013.01); *A61K 31/4045* (2013.01); *A61K 36/71* (2013.01); *A61K 47/32* (2013.01); *A61M 35/00* (2013.01); *A61P 5/24* (2018.01); *A61P 25/32* (2018.01); *A61P 43/00* (2018.01); *A61F 2013/0296* (2013.01)

(58) Field of Classification Search
None
See application file for complete search history.

(56) References Cited

U.S. PATENT DOCUMENTS

| | | | | |
|---|---|---|---|---|
| 2011/0052694 | A1* | 3/2011 | Stinchcomb | A61K 9/0021 424/484 |
| 2016/0022627 | A2* | 1/2016 | Smith | A61K 31/352 424/449 |

FOREIGN PATENT DOCUMENTS

| | | | | |
|---|---|---|---|---|
| WO | WO-2008053481 A1 * | 5/2008 | | A61M 37/0015 |
| WO | WO-2016167545 A1 * | 10/2016 | | A61K 9/00 |

OTHER PUBLICATIONS

C. I. Bih, T. Chen, A. V. W. Nunn, M. Bazelot, M. Dallas, and B. J. Whalley. Molecular Targets of Cannabidiol in Neurological Disorders. Neurotherapeutics (2015) 12:699-730 (Year: 2015).*
Scifinder Search Jan. 17, 2020 (Year: 2020).*

* cited by examiner

*Primary Examiner* — Michael P Cohen
(74) *Attorney, Agent, or Firm* — Patnstr®, APC; Tom Brody; Peter Jon Gluck, Esq.

(57) ABSTRACT

The disclosure provides dermal patch formulations that include a pharmaceutically active agent, such as one or more cannabinoids. The formulations can include dihydromyricetin for the purpose of increasing the flux of the pharmaceutical agent into human skin.

8 Claims, 2 Drawing Sheets

DIHYDROMYRICETIN COMPOSITIONS

PRIORITY BENEFIT

This application claims the benefit of and priority to U.S. Provisional Patent Application Ser. No. 62/624,596, filed Jan. 31, 2018, the content of which is incorporated herein by reference herein in its entirety.

FIELD OF THE DISCLOSURE

The disclosure relates to dermal patches, sublingual patches, buccal patches, each of which contains a formulation providing a pharmaceutical agent such as a drug or a nutraceutical in combination with dihydromyricetin, or a pharmacologically active derivative or breakdown product of dihydromyricetin. The drug can be one or more cannabinoids.

BACKGROUND OF THE DISCLOSURE

Dermal patches can take the form of a monolithic-style patch or a reservoir-style patch (Ser. No. 15/265,823, US 2017/0071870 of Weimann, which is incorporated herein in its entirety). Monolithic-style patch can take the form of a sandwich, where the face that is exposed to the atmosphere takes the form of a backing, where the opposite face takes the form of a release liner, and where the filling of the sandwich is a matrix that includes an adhesive and a pharmaceutical agent such as a drug or nutraceutical. Prior to applying the patch to the skin, a release liner is removed and discarded. The reservoir of a reservoir patch includes pharmaceutical agent such as a drug or nutraceutical. Reservoir-style devices require an additional adhesive coated overlay to hold the device in place on the wearer's skin.

In addition to containing a drug or nutraceutical, the reservoir of the reservoir patch also contains a liquid carrier and a gelling agent. The reservoir can be defined by a backing and by a permeable membrane, which together assume a "ravioli" conformation. The permeable membrane is optionally coated with an adhesive that mediates binding of the adhesive to the skin. On one side of the adhesive is the permeable membrane, and on the other side is a release liner. Prior to applying the patch to the skin, a release liner is removed and discarded.

The present disclosure addresses the need for chemicals and other substances that can enhance passage of an active pharmaceutical agent through the skin, where the site of pharmaceutical action is in the skin itself, or for enhancing passage of an active pharmaceutical agent through the skin and to the bloodstream, where the site of pharmaceutical action is at locations in the body remote from the site of attachment of the dermal patch.

BRIEF DESCRIPTIONS OF THE DRAWINGS

Figure 1:
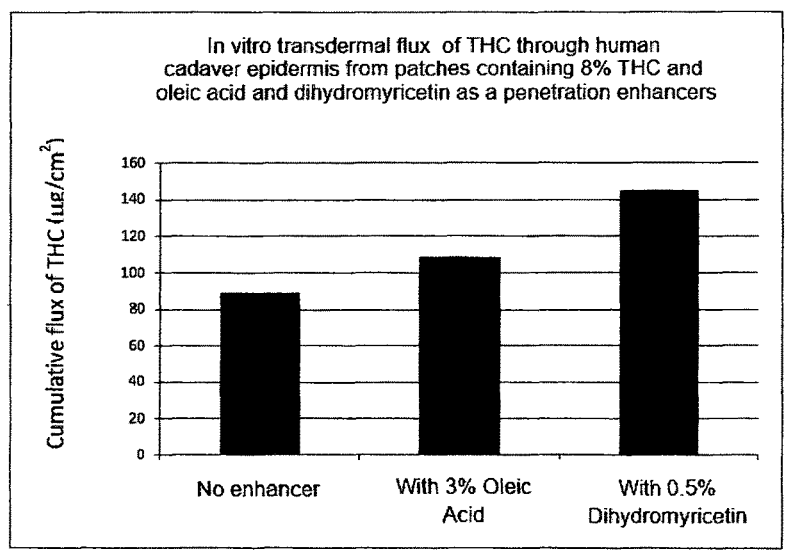

FIG. 1. In vitro transdermal flux of THC through human cadaver epidermis from patches containing 8% THC and either, no enhancer (first bar), 3% oleic acid (second bar), or 0.5% dihydromyricetin. The value shows cumulative flux.

Figure 2:
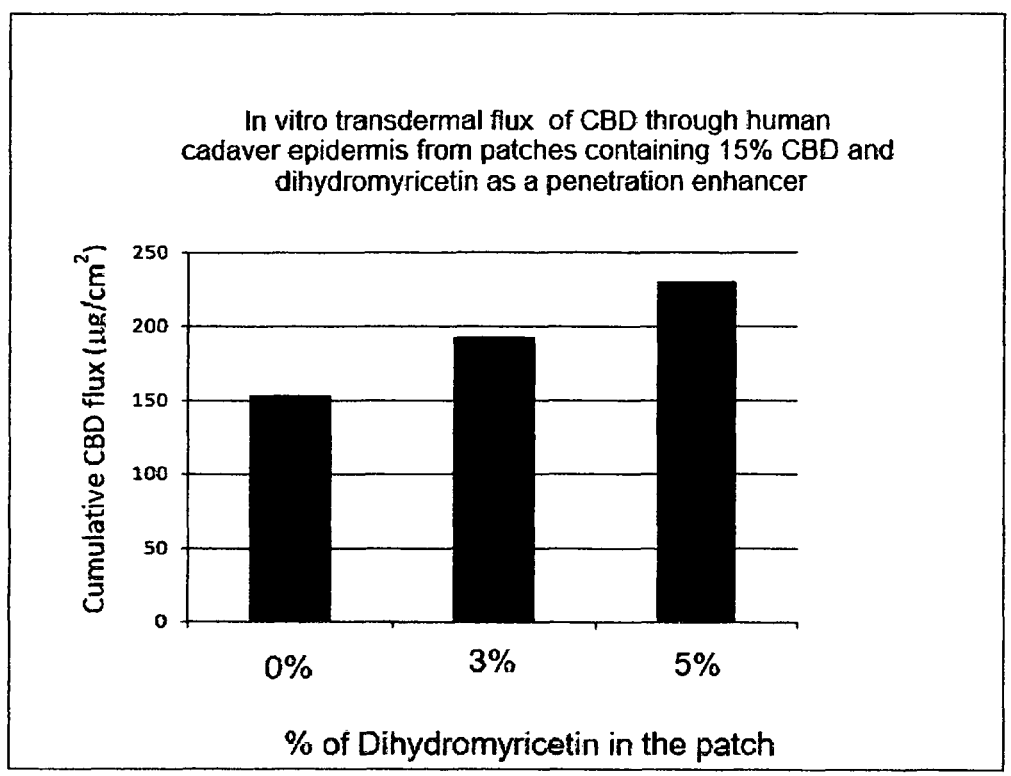

FIG. 2. In vitro transdermal flux of CBD through human cadaver epidermis from patches containing 15% CBD and dihydromyricetin as a penetration enhancer, with either 0% dihydromyricetin (first bar), 3% dihydromyricetin (second bar), or 5% dihydromyricetin (third bar). The value shows cumulative flux.

SUMMARY OF THE DISCLOSURE

The present disclosure provides a monolithic patch that comprises polyisobutylene (PIB) adhesive, with dihydromyricetin, and with 15% of cannabidiol (CBD), wherein the construction comprises an adhesive layer attached to a backing, and wherein the monolithic patch is capable of delivering at CBD at a net flux of at least 195 micrograms CBD per square centimeter of skin over a period of 24 hours, as compared to a control net flux of about 155 micrograms CBD per square centimeter of skin over a period of 24 hours for a control monolithic patch that does not contain any dihydromyricetin.

Also provided is the above monolithic patch, wherein the backing comprises polyethylene foam film. Moreover, what is provided is the above monolithic patch that does not contain any type of overlay that is in addition to the polyethylene foam film. In another aspect, what is provided is the above monolithic patch, wherein the cannabinoid flux is measured or is measurable with a Franz diffusion cell and human cadaver skin. Also embraced, is the above monolithic patch, that does not comprise any enhancer aside from dihydromyricetin. Also provided is the above monolithic patch, that does not comprise any combination of, azone, oleic acid, a terpene, and ethanol. In yet another aspect, what is provided is the above monolithic patch, that does not comprise one or more of, azone, oleic acid, a terpene, and ethanol. Also embraced is the above monolithic patch, wherein the only cannabinoid present is CBD. Tn yet another aspect, what is provided is the above monolithic patch, wherein the dihydromyricetin concentration is about 0.5%, about 1.0%, about 2.0%, about 3.0%, about 4.0%, or about 5.0% dihydromyricetin.

In THC embodiments, what is provided is a monolithic patch that comprises polyisobutylene (PIB) adhesive, with dihydromyricetin, and with 8% tetrahydrocannabinol (THC), wherein the construction comprises an adhesive layer attached to a backing, and wherein the monolithic patch is capable of delivering at THC at a net flux of at least 145 micrograms THC per square centimeter of skin over a period of 24 hours, as compared to a control net flux of about 90 micrograms THC per square centimeter of skin over a period of 24 hours for a control monolithic patch that does not contain any dihydromyricetin. In another THC embodiment, what is provided is the above monolithic patch, wherein the backing comprises polyethylene foam film. Moreover, what is provided is the above monolithic patch that does not contain any type of overlay that is in addition to the polyethylene foam film. Also embraced is the above monolithic patch, wherein the cannabinoid flux is measured or is measurable with a Franz diffusion cell and human cadaver skin. Further contemplated is the above monolithic patch, that does not comprise any enhancer aside from dihydromyricetin. Also, what is provided is the above monolithic patch, that does not comprise any combination of, azone, oleic acid, a terpene, and ethanol. Also, what is provided is the above monolithic patch that does not comprise one or more of, azone, oleic acid, a terpene, and ethanol. In yet another aspect, what is embraced is the above monolithic patch wherein the only cannabinoid present is THC. Also, what is provided is the above monolithic patch, wherein the dihydromyricetin concentration is about 0.5%, about 1.0%, about 2.0%, about 3.0%, about 4.0%, or about 5.0% dihydromyricetin.

In combination embodiments, the patch contains cannabinoids that include THC and CBD. In other cannabinoid embodiments, the patch contains cannabinoids that are only THC and CBD.

In methods embodiments, what is provided is a method for using one of the above monolithic patches, wherein the method comprises attaching, contacting, or adhering the above monolithic patch to the skin of a living human being, and the step of allowing at least 0.5% of the cannabinoid in the patch, or at least 1.0%, or at least 2%, or at least 5%, or at least 10%, to soak into or to pass into the skin.

Where a formulation contains a plurality of ingredients, the relative amounts of the ingredients can be defined in terms of the proportions of each ingredient in that formulation. Alternatively, the relative amounts of the ingredients can be defined in terms of the ratios of the ingredients, relative to each other. For example, where a formulation contains ingredient A and ingredient B, it is understood that "ratio" can refer to the ratio of A/B. Also, for example, where a formulation contains ingredient A, ingredient B, and ingredient C, the term "ratio" can refer to the ratio of A/C and the ratio of B/C. As an example of the use of the term "proportion," the present disclosure provides a formulation comprising a plurality of active ingredients, and one or more inactive ingredients, wherein a dermal patch comprising the formulation is capable of delivering cannabidiol into human skin, and wherein the proportions of said plurality of active ingredients relative to each other are the proportions that are set forth by: Active ingredients cannabidiol (about 15 mg); menthol (about 6 mg), camphor (about 1.5 mg), wherein the formulation also includes one or more of the inactive ingredients synthetic rubber polymer, polyester terephthalate, and polyethylene. As an example with use of the term "ratio," the present disclosure provides a formulation comprising a plurality of active ingredients, and one or more inactive ingredients, wherein a dermal patch comprising the formulation is capable of delivering cannabidiol into human skin, and wherein the ratio of said plurality of active ingredients to each other conforms to a weight/weight ratio, that is as set forth by: Active ingredients cannabidiol (about 15 mg); menthol (about 6 mg), camphor (about 1.5 mg), wherein the formulation also includes one or more of the inactive ingredients synthetic rubber polymer, polyester terephthalate, and polyethylene.

The present disclosure provides a formulation comprising a plurality of active ingredients, and one or more inactive ingredients, wherein a dermal patch comprising the formulation is capable of delivering cannabidiol into human skin, and wherein the ratio of said plurality of active ingredients to each other conforms to a weight/weight ratio, that is as set forth by one of:

i. Active ingredients cannabidiol (about 15 mg); menthol (about 6 mg), camphor (about 1.5 mg), wherein the formulation also includes one or more of the inactive ingredients synthetic rubber polymer, polyester terephthalaic, and polyethylene; or ii. Active ingredients cannabidiol (about 15 mg); soy isoflavones extract (about 5 mg), black cohosh extract (about 5 mg), menthol (about 6 mg), camphor (about 1.5 mg), and wherein the formulation also includes one or more of the inactive ingredients synthetic rubber polymer, polyester terephthalate, and polyethylene, or iii. Active ingredients cannabidiol (about 15 mg); dihydromyricetin (about 8 mg), and wherein the formulation also includes one or more of the inactive ingredients synthetic rubber polymer, polyester terephthalate, and polyethylene; or iv. Active ingredients cannabidiol (about 15 mg); melatonin (about 6 mg), and wherein the formulation also includes one or more of the inactive ingredients synthetic rubber polymer, polyester terephthalate, and polyethylene.

In embodiments where the values for the ratios are more exact, the present disclosure encompasses the above formulation, comprising a plurality of active ingredients, and one or more inactive ingredients, wherein a dermal patch comprising the formulation is capable of delivering cannabidiol into human skin, and wherein the ratio of said plurality of active ingredients to each other conforms to a weight/weight ratio that is as set forth by one of:

i. Active ingredients cannabidiol (15 mg); menthol (6 mg), camphor (1.5 mg), and wherein the formulation also includes one or more of the inactive ingredients, synthetic rubber polymer, polyester terephthalate, and polyethylene; or ii. Active ingredients cannabidiol (15 mg); soy isoflavones extract (5 mg), black cohosh extract (5 mg), menthol (6 mg), camphor (1.5 mg), and wherein the formulation also includes one or more of the inactive ingredients, synthetic rubber polymer, polyester terephthalate, and polyethylene, or iii. Active ingredients cannabidiol (15 mg); dihydromyricetin (8 mg), and wherein the formulation also includes one or more of the inactive ingredients, synthetic rubber polymer, polyester terephthalate, and polyethylene; or iv. Active ingredients cannabidiol (15 mg); melatonin (6 mg), and wherein the formulation also includes one or more of the inactive ingredients, synthetic rubber polymer, polyester terephthalate, and polyethylene.

In dihydromyricetin embodiments, the present disclosure provides the above formulation, comprising dihydromyricetin, wherein the dihydromyricetin is in an amount that is capable of increasing flux of the cannabidiol into human skin, or wherein the dihydromyricetin/cannabidiol ratio is at a ratio that is capable of increasing flux of the cannabidiol into human skin, wherein said capable of increasing flux is with respect to flux obtained with a comparator formulation wherein dihydromyricetin is replaced by an equivalent weight of a pharmacologically inert chemical that does not influence the rate of cannabidiol flux. Also encompassed is the above formulation wherein the cannabidiol is hemp cannabidiol.

In dermal patch embodiments, the present disclosure contemplates a dermal patch that comprises a formulation that comprises one or more active ingredients, and one or more inactive ingredients, wherein the dermal patch comprising the formulation is capable of delivering cannabidiol into human skin, and wherein the ratio of said plurality of active ingredients to each other conforms to a weight/weight ratio that is as set forth by one of:

i. Active ingredients cannabidiol (about 15 mg); menthol (about 6 mg), camphor (about 1.5 mg), and the wherein the formulation also includes one or more of the inactive ingredients synthetic rubber polymer, polyester terephthalate, and polyethylene; or ii. Active ingredients cannabidiol (about 15 mg); soy isoflavones extract (about 5 mg), black cohosh extract (about 5 mg), menthol (about 6 mg), camphor (about 1.5 mg), and wherein the formulation also includes one or more of the inactive ingredients synthetic rubber polymer, polyester terephthalate, and polyethylene, or iii. Active ingredients cannabidiol (15 mg); dihydromyricetin (8 mg), and the inactive ingredients: synthetic rubber polymer, polyester terephthalate, polyethylene; or iv. Active ingredients hemp cannabidiol (15 mg); melatonin (6 mg), and wherein the formulation also includes one or more of the inactive ingredients synthetic rubber polymer, polyester terephthalate, and polyethylene. Also provided, is the above dermal patch that is a monolithic patch. Moreover, what is further provided is the above dermal patch that is a reservoir patch.

The present disclosure also provides methods for manufacturing a monolithic dermal patch or a reservoir patch comprising one of the above-identified formulations. Also encompassed is a method for medical use of a monolithic dermal patch or a reservoir patch that comprises one of the above formulations, wherein the method comprises placing the dermal patch on the skin of a human subject.

DETAILED DESCRIPTION

As used herein, including the appended claims, the singular forms of words such as "a," "an," and "the" include their corresponding plural references unless the context clearly dictates otherwise. All references cited herein are incorporated by reference to the same extent as if each individual patent, and published patent application, as well as figures, drawings, sequence listings, compact discs, and the like, was specifically and individually indicated to be incorporated by reference.

This provides non-limiting descriptions of the meaning that a given composition "does not contain any" amount of a given chemical. The meaning could be, "beyond the lower level of detection," for example, by way of an instrument such as a spectrophotometer. Where the composition is a powder, oil, fluid, liquid, aqueous solution, slurry, paste, or suspension, and the like, the meaning could be, less than 1.0%, less than 0.2%, less than 0.1%, less than 0.02%, less than 0.01%, less than 0.002%, less than 0.001%, less than 0.0002%, less than 0.0001%, or less than 0.00002% of the total volume of the composition. Also, where the composition is a powder, oil, fluid, liquid, aqueous solution, slurry, paste, or suspension, and the like, the meaning could be, less than 1.0%, less than 0.2%, less than 0.1%, less than 0.02%, less than 0.01%, less than 0.002%, less than 0.001%, less than 0.0002%, less than 0.0001%, or less than 0.00002% of the total weight of the composition.

PATCH EMBODIMENTS

The present disclosure provides a composition capable of use in a dermal patch, buccal patch, sublingual patch, pill, tablet, and so on, where the composition comprises dihydromyreticin and a cannahinoid. Dihydromyrecitin is available from Sigma-Aldrich, St. Louis, Mo.

In embodiments, the disclosure provides compositions that also comprise one or more of, an acrylic adhesive with non-functionality and an adhesive with only OH-functionality, further comprising one of more of enhancers selected from azone (azone is "1-dodecyl azepan-2-one"), oleic acid, and dimethylsulfoxide (DMSO); a polyisobutylene (PIB adhesive) with tackifiers that improve adhesion to skin using acrylic pressure sensitive adhesive mixed in at 1-50%, optionally with a cycloaliphatic hydrocarbon resin; a PIB adhesive with enhancers: at 3% of azone or oleic acid double the transdermal delivery from PIB; hemp oil with CBD of concentration 80-95% containing at least one terpene; a semisolid hydrogel that is saturated with cannabidiol (CBD) and tetrahydrocannabinol (THC); a semisolid hydrogel comprising an oil that consists essentially of CBD and THC (80-95%, wt/vol), in combination with ethanol/water (80/20, vol/vol), optionally with one or more enhancers selected from azone, oleic acid, and limonene; a semisolid hydrogel saturated with CBD and THC oils (80-95%, wt/vol), wherein the oil is mixed with EtOH/water (80/20, vol/vol), optionally with one or more enhancers selected from azone, oleic acid, and limonene; or a THC oil of THC (80-95%) mixed with 1-20% EtOH or with 1-10% EtOH/water (80/20, vol/vol) wherein including greater than 10% of ethanol is capable of lowering flux of THC delivery as determinable with a reservoir patch. Also provided is a dermal monolithic patch, a dermal reservoir patch, a buccal patch, a sublingual pill, a sublingual tablet, or sublingual patch, comprising one of the above compositions.

Also provided, is a method for applying the above dermal patch to skin of a human subject, and allowing a cannabinoid to transit from the dermal patch into the skin of the human subject. In another aspect, what is provided is a method for applying the above buccal patch to the buccal mucosa of a human subject, and allowing a cannabinoid to transit from the buccal patch into the buccal mucosa of the human subject.

The present disclosure also provides a method for manufacturing a dermal patch, comprising the steps of combining dihydromyricetin, a cannabinoid, such as THC, an adhesive (or alternatively, an overlay), and a backing, to generate an uncut patch, further comprising the cutting the uncut patch to produce a cut patch that is capable of applying to human skin or of applying to human buccal pouch.

Suppliers, Detection, and Quantification of Dihydromyricetin (DHM)

Dihydromyricetin (DHM) can be detected and quantified by high pressure liquid chromatography (HPLC), such as with 1260 Infinity series HPLC (Agilent Technologies, Richmond, Va.) with an Agilent Porshell HC-C18 column. Dihydromyricetin can be identified by MALDI-TOF using, for example, Autoflex Speed MALDI-TOF, Bruker Daltonics, Bremen, Germany (see, Muhammad et al (2017) Optimizing the maximum recovery of dihydromyricetin from Chinese vine tea. Molecules. 22, 2250; doi: 10.3390).

The present disclosure provides DHM analogues, for example, for use in increasing cannabinoid transfer from a dermal patch to the skin, and for use in increasing transfer followed by absorption into the skin. DHM analogues include, for example, (2S,3S)-5-methyldihydromyricetin, (2S,3S)-5-methyldihydromyricetin-3'-O-sulfate and β-D-glucopyranoside, 3-methyl, but-3-en-1-yl 4-O-α-L-rhamnopyranosyl, and dihydromyricetin-3'-O-sulfate, myricetin-3'-O-sulfate, 5-methylmyricetin, myricetin, myricetin-3-O-β-glucoside (see, Gadetskaya et al (2015) Filoterapia. 104: 80-85). Another DHM analogue is (+)-gallocatechin (2,3-trans3,5,7,3',4',5'-hexahydroxy-flavan) (see, Stafford and Lester (1985) Plant Physiol. 78:791-794). In exclusionary embodiments, the present disclosure can exclude any composition, solution, dermal patch, or medical device, that contains one or more of the above DHM metabolites and DHM analogues.

The present disclosure provides combinations of two or more DHM analogues, as well as combinations of DHM with one or more DHM analogues.

Cannabinoids and Treatment of Conditions and Disorders

The present disclosure provides dermal patches, formulations, dermal patches not containing a formulation, and dermal patches including a formulation. Preferred formulations include one or more cannabinoids. The major cannabinoids from Cannabis sativa are cannabidiol (CBD), cannabichromene (CBC), cannabigerol (CBG), delta-9-tetrahydrocannabinol (delta-9-THC), and cannabinol (CBN)

(Appendino et al (2008.) J. Nat. Prod. 71:1427-1430). Clinical trials have established that formulations derived from cannabis, can improve neuropathic pain of multiple sclerosis, improve appetite and sleep quality in cancer patients, relieve pain in fibromyalgia patients, and serve as an anti-emetic for chemotherapy induced nausea and vomiting (see, Health Canada (February 2013) Information for Health Care Professionals. Cannabis (Marihuana, Marijuana) and the Cannabinoids (152 pages)). Cannabinoids have been reported to result in improvements in sleep and relief from insomnia (see, Abrams (2016) Current Oncology. 23:S8-S14). Also, cannabinoids have been reported to relieve premenstrual syndrome (PMS) (see, Slavin et al (2017) Cannabis and symptoms of PMS and PMDD. Addiction Research and Theory. 25:1-7).

This concerns scoring of conditions and disorders, and for assessing the influence of cannabinoids on these conditions and disorders. Severity of symptoms of premenstrual syndrome (PMS) can be assessed with a scoring questionnaire (see, Retallick-Brown (2016) Medicines (Basal). 7:32; doi: 10.3390; Endicott (2006) Daily Record of Severity Problems (DRSP): Reliability and validity. Arch. Women Health. (41-49). Insomnia and sleep quality can be scored by actigraphy scoring, by polysomnograph, and by sleep logs (see, Kapella (2017) Sleep Med. 37:124-129). Sleep onset latency (SOL), time spent awake time after sleep onset (WASO), and sleep efficiency (SE) can be measured with sleep logs (Roeser (2016) J. Clinical Sleep Medicine. 12:257-262). Headaches can be assessed and scored, for example, by Migraine Disability Assessment (MIDAS) questionnaire, Impact of Migraine on Partners and Adolescent Children (IMPAC) questionnaire, (see, Lipton (2017) Headache. 57:570-585). Also, a verbal numerical rating scale of 0-10 can be used to assess the degree of headache, with 0/10 indicating no headache and 10/10 indicating the worst headache imaginable (see, Amin et al (2008) Cephalalgia. 28:355-359). Headache Impact Test is also available (see, Wei, Jia, Wang (2016) Chinese Medical Journal. 129:1394-1399).

In response to injury or disease the brain expresses endogenous cannabinoids. After closed head injury, higher levels of the endogenous cannabinoid 2-AG (2-arachidonoyl glycerol) are associated with decreased edema, smaller infarct volume, and reduced hippocampal cell death. Administration of Δ9-tetrahydrocannabinol (THC), reduces neuronal death and counter cytotoxic changes in the brains with exposure to various neurotoxic compounds (see, Mahmood et al (2010) J. Stud. Alcohol Drugs. 71:885-894). Moreover, evidence indicates that cannabis provides a neuroprotective role in attenuating the negative effects of heavy alcohol use (see, Mahmood et al (2010) J. Stud. Alcohol Drugs. 71:885-894).

The present disclosure also provides tetrahydrocannabinovarin (THCV), which is a propyl analogue of THC, and cannabidivarin (CBDV), which is a propyl analogue of CBD.

Formulations and compositions that include both THC and CBD at a given ratio are provided, such as at the ratio of about 95/5, about 90/10, about 80/20, about 70/30, about 60/40, about 50/50, about 40/60, about 30/70, about 20/80, about 10/90, and about 5/95 (by weight). Administering formulations containing both THC and CBD can have greater influence on reducing pain that formulations containing only THC or only placebo (see, Johnson et al (2010) J. Pain Symptom Management. 39:167-179; Notcutt et al (2004) Anaesthesia. 5944-452).

One of more of the following cannabinoids can be included in the compositions of the present disclosure. Cannaboids and related compounds further include, for example, cannabichromene; cannabitriol; cannabicyclolol; cannabielsoin, cannabinodiol; delta-8-tetrahydrocannabinol; cannabichromanone; cannabicoumaronone; cannabicitran; 10-oxo-delta-6a10a-tetrahydrocannabinol; cannabiglendol; delta-7-isotetrahydrocannabinol; CBLVA; CBV; CBEVA-B; CBCVA; delta-9-THCVA; CBDVA; CBGVA; divarinolic acid; quercetin; kaemferol; dihydrokaempferol; dihydroquercetin; cannflavin B; isovitexin; apigenin; naringenin; eriodictyol; luteolin; orientin; cytisoside; vitexin; canniprene; 3,4'-dihydroxy-5-methoxy bibenzyl; dihydroresveratrol; 3,4'-dihydroxy-5,3'-dimethoxy-5'-isoprenyl; cannabistilbene 1; cannabistilbene 11a; cannabistilbene 11b; cannithrene 1; cannithrene 2; cannabispirone; iso-cannabispirone; cannabispirenon-A; cannabispirenone-B; cannabispiradienone; alpha-cannabispiranol; beta-cannabispiranol; acetyl-cannabispirol; 7-hydroxy-5-methoxyindan-1-spiro-cyclohexane; 5-hydroxy-7-methoxyindan-1-spiro cyclohexane; myristic acid, palmitic acid, oleic acid, stearic acid, linoleic acid, linolenic acid, arachidic acid, eicosenoic acid, behenic acid, lignoceric acid, 5,7-dihydroxyindan-1-cyclohexane; cannabispiradienone; 3,4'-dihydroxy-5-methoxybibenzyl; canniprene; cannabispirone; cannithrene I; cannithrene 2; alpha-cannabispiranol; acetyl-cannabispirol; vomifoliol; dihydrovomifoliol; beta-ionone; dihydroactinidiolide; palustrine; palustridine; plus-cannabisativine; anhydrocannabisativine; dihydroperiphylline; cannabisin-A; cannabisin-B; cannabisin-C; cannabisin-D; grossamide; cannabisin-E; cannabisin-F; cannabisin-G; and so on (see, e.g., Flores-Sanchez and Verpoorte (2008) Secondary metabolism in cannabis. Phytochem. Rev. 7:615-639).

In exclusionary embodiments, the present disclosure can exclude any formulation, composition, device, or method that comprises CBD, CBC), CBG, delta-9-THC, CBN, or any chemical in the above list. What can be excluded is any formulation, composition, device, or method, that takes the form of a liquid cannabinoid formulation where at least 20%, at least 40%, at least 60%, at least 80%, at least 90%, or at least 95%, of total cannabinoids is tetrahydrocannabinolic acid (THCa). Also, what can be excluded is any formulation, composition, device, or method, that takes the form of an oil formulation, where the oil formulation contains one or more cannabinoids, where at least 20%, at least 40%, at least 60%, at least 80%, at least 90%, at least 95% of total cannabinoids is tetrahydrocannabinolic acid (THCa).

MEASURING CANNABINOIDS

Cannabinoids can be separated, purified, analyzed, and quantified by a number of techniques. Available equipment and methods include, e.g., gas chromatography, HPLC (high pressure liquid chromatography, high performance liquid chromatography), mass spectrometry, time-of-flight mass spectrometry, gas chromatography-mass spectrometry (GC-MS), and liquid chromatography-mass spectrometry (LC-MS). Equipment for separation and analysis is available from Waters Corp., Milford, Mass.; Agilent, Foster City, Calif.; Applied Biosystems, Foster City, Calif.; and Bio-Rad Corp., Hercules, Calif. Methods, equipment, and manufacturers for HPLC fractionation and identification of cannabinoids are disclosed (see, e.g., Peschel W (2016) Quality control of traditional cannabis tinctures. Sci. Pharm. 84:567-584; Scheidweiler K B et al (2012) Simultaneous quantification of free and glucuronidated cannabinoids in human urine by liquidchromatography tandem mass spectrometry. Clin. Chim. Acta. 413:1839-1847).

The present disclosure provides in-line monitoring of purification, that is, quantitation of THC as well as quantitation of impurities. In-line monitoring may be by UPLC methods, or by other methods. Ultra-high performance liquid chromatography (UPLC) is similar to HPLC, except that UPLC uses smaller particles in the column bed, and greater pressures. The particles can be under 2 micrometers in diameter, and pressures can be nearly 15,000 psi. UPLC also uses higher flow rates, and can provide superior resolution and run times in the range of under 30 seconds (Wren and Tchelitcheff (2006) J. Chromatography A. 1119:140-146; Swartz, M. E. (May 2005) Separation Science Redefined). The application of UPLC to cannabinoids has been described (see, Jamey et al (2008) J. Analytical Toxicology. 32:349-354; Badawi et al (2009) Clinical Chemistry. 55:2004-2018). Suitable UPLC columns for cannabinoid analysis include, e.g., Acquity®UPLC HSS T3 C18, and Acquity® UPLC BEH C18 column (Waters, Milford, Mass.). Other methods for detecting cannabinoids include, e.g., infrared (IR) spectroscopy, gas chromatography mass spectroscopy (GCMS), and electrospray tandem mass spectroscopy (ESI-MS/MS) (Ernst et al (2012) Forensic Sci. Int. 222:216-222).

Biochemical properties of cannabinoids, binding to cannabinoid receptors, terpenes and terpene receptor binding, can be assessed using labeled cannabinoids, labeled terpenes, and labeled ligands where a cannabinoid or a terpene influences binding properties of the labeled ligand. Useful labels include radioactive labels, epitope tags, fluorescent dyes, electron-dense reagents, substrates, or enzymes, e.g., as used in enzyme-linked immunoassays, or fluorettes (see, e.g., Rozinov and Nolan (1998) Chem. Biol. 5:713-728).

Cannabinoid Numbering Systems

The present disclosure uses the nomenclature as set forth by Pertwee R G et al (2010) International Union of Basic and Clinical Pharmacology. LXXIX, Cannabinoid receptors and their ligands: beyond CB1 and CB1, Pharmacol. Rev. 62:588-631. Regarding different numbering systems for the same compound, Aviv (US 2004/0110827) states that: "It should be noted that for historical reasons, these cannabinoid analogs are still named following the previous nomenclature, where the terpenic ring was the base for the numbering system. Then the chiral centers of THC type cannabinoids were at carbon atoms 3 and 4. The accepted nomenclature is now based on the phenolic ring as the starting point for numbering. Thus, THC that was previously described as delta-1-THC was later renamed delta-9-THC, similarly delta-6-THC was renamed delta-8-THC, and the chiral centers are at carbons 6a and 10a." AVIV also has this comment about enantiomers: "delta-9-THC was established by Mechoulam R. et al. in 1967 and found to be of (−)-(3R,4R) stereochemistry. It was later found that the psychotropic activity of cannabinoids resides in the natural (3R,4R) OH series, while the opposite enantiomeric synthetic series (3S,4S) was free of these undesirable effects."

According to Agurell (1988) Pharmacological Revs. 38:21-43, the terpene numbering system uses delta-1-THC, while the dibenzopyran system uses delta-9-THC to refer to the same chemical. Both of these numbering systems can be used for THC, CBD, and CBN.

According to Chulgin, the numbering system most broadly used recognizes both the terpene nature and the aromatic nature of the two different parts of the cannabinoid. Here, the terpene is numbered from the ringcarbon that carries that branched, methyl group, and this is numbered 7, and the remaining three carbons of the isopropyl group are then numbered sequentially. The advantage to this numbering system is that this numbering system is applicable whether the center ring is closed or open. Other numbering systems are the biphenyl numbering system, the Chemical Abstracts system (substituted dibenzopyran numbering), and the Todd numbering system (pyran numbering) (see, Chulgin AT (1969) Recent developments in cannabis chemistry. J. Psychedelic Drugs, pp. 397-415.

Hemp Oil, Other Oils, and Extracts

Hemp oil or hempseed oil is obtained by pressing hemp seeds. It is an edible oil that contains about 80% of essential fatty acids but it is not CBD hemp oil.

Cannabidiol (CBD) hemp oil can be manufactured using Supercritical Carbon Dioxide ($CO_2$) extraction of the stalk of the industrial hemp plant. CBD hemp oil usually contain 20-40% CBD. To produce crystalline CBD of 99.8% pure, the CBD oil is processed further using fractional distillation.

Marijuana extract oils are extracts of marijuana plants such as Sativa or Indica. The extracts are solids or semisolids of different % of CBD, THC and other cannabinoids. Marijuana THC extracts (oils) may have high % of THC up to 80% and some CBD about 10-20%.

Marijuana CBD extracts may have high % of CBD up to 90% and low % of THC up to 10%. The percentage of cannabinoids in the marijuana extracts depend on the content of those substances in marijuana plants that are used in extraction. Extraction are done by using butane, ethyl alcohol or critical $CO_2$ extraction.

Hemp oil suppliers are listed here (see, e.g., Medical Marijuana, Inc., Poway, Calif.; Nutiva, Richmond, Calif.; Entourage Nutritional Distributors, Colorado Springs, Calif.). Hemp ground in Poland, for example, has been described (see, e.g., L. Grabowska et al (2009) Breeding and cultivation of industrial hemp in Poland. Herba Polonica. 55:328-334; L. Grabowska et al (2008) Maintenance breeding of Polish hemp cultivar Beniko. J. Natural Fibers. 5:208-217). Varieties (cultivars) of hemp grown in Poland and adapted to Polish climate and soil conditions include, Bialobrzeskie, Beniko, Silesia, Tygra, and Wielkopolskie.

Since CBD hemp oil can be produced without stripping it from terpenes, the transdermal formulation of the present disclosure provides information if the natural terpenes facilitate the transdermal skin penetration of CBD and information on how the natural terpenes provide medicinal properties once absorbed through the skin.

Matrix Embodiments

An excipient useful for granulating agents and sprays is the polyvinylpyrrolidone copolymer having a given ratio, or range of ratios, of polyvinylpyrrolidone/vinyl acetate (PVP/VA). The present disclosure provides PVP/VA (or combinations of any two polymers), at a ratio of 10/90, 20/80, 30/70, 40/60, 50/50, 60/40, 70/30, 80/20, 90/10, as well as a combination of any two polymer at a ratio of about 10/90, about 20/80, about 30/70, about 40/60, about 50/50, about 60/40, about 70/30, about 80/20, about 90/10. Also, the present disclosure can exclude PVP/VA compositions (or it can exclude a combination of any two polymers) with a ratio of, 10/90, 20/80, 30/70, 40/60, 50/50, 60/40, 70/30, 80/20, 90/10, or about 10/90, about 20/80, about 30/70, about 40/60, about 50/50, about 60/40, about 70/30, about 80/20, about 90/10, and the like. The PVP/VA copolymer has the ability to distribute homogeneously around an active ingredient during formation of an aqueous liquid phase (see, US 2016/0058866 of Sekura). Polymers and copolymers are available from Sigma-Aldrich, St. Louis, Mo., Nippon Shokubai Co., Ltd., Osaka, Japan, BASF Corp., Florham Park, N.J., and Ashland, Schaffhausen, Switzerland.

A laminate that can be held in place on the gingiva (gums) takes the form of a semipermeable outer layer, reservoir having a pharmaceutical, backing layer, where the backing layer faces the gingiva. Saliva can enter through the semipermeable outer layer, pass through the reservoir, and then draw medicine into contact with gingiva for absorption in the bloodstream. A pharmaceutical can be freeze dried or can occur as a hydrogel matrix, in the reservoir. The present disclosure provides a backing layer of one or more polymers, such as, ethyl cellulose, butyl cellulose, hydroxybutyl cellulose, or polyvinylalcohol. An amorphous or semi-crystalline excipient matrix can be made from methylcellulose, ethyl cellulose, hydroxypropyl methylcellulose, cellulose acetate phthalate, or cellulose acetate butyrate. In exclusionary embodiments, the present disclosure can exclude one or more of these polymers.

In reservoir-distribution embodiments, a pharmaceutical or nutraecutical can be distributed evenly throughout reservoir, or can be distributed at a higher concentration at center of reservoir, or can be distributed at a higher concentration at region of reservoir that is closer to the skin when patch is situated and adhering to skin.

Tackifiers

The present disclosure provides compositions, patches, and methods, that encompass one or more of Escorez 1000 Series-aliphatic resins; Escorez 2000 Series-aromatic modified aliphatic resins; Escorez 5300 Series-water white hydrogenated cycloaliphatic resins; Escorez 5400 Series-light color hydrogenated cycloaliphatic resins; Escorez 5600 Series-light color hydrogenated aromatic modified cycloaliphatic resins; Escorene® Ultra ethylene vinyl acetate (EVA) copolymers; ExxonMobil® ethylene n-butyl acrylate (EnBA) copolymers; Optema® EMA (ethyl methyl acrylate) resins (ExxonMobil, Inc.).

Escorez® 5400 is a hydrocarbon polymer additive available from ExxonMobil Chemical Company. It has a softening point of 103° C. a weight average moiccuiar weight of about 400 g/mole, and a dicyclopentadiene/cyclopentadiene/methylcyclopentadiene content of 40-80 wt % (see, WO2013/176712 of Block).

Escorez® 5415 is a hydrocarbon polymer additive available from ExxonMobil Chcmieal Company. It has a softening point of 118° C., a weight average molecular weight of about 430 g/mole, and a dicyclopentadiene/cyclopentadiene/methylcyclopentadiene content of 40-80 wt % (see, WO2013/176712 of Block).

Escorez® 5340 is a hydrocarbon polymer additive available from ExxonMobil Chemical Company. It has a softening point of 140° C. a weight average molecular weight of about 460 g/mole, and a dicyclopentadiene/cyclopentadiene/methylcyclopentadiene content of 40-80 wt % (see, WO2013/176712 of Block).

Escorez® 5600 is a hydrocarbon polymer additive available from ExxonMobil Chemical Company. It has a softening point of 103° C., a weight average molecular weight of about 520 g/mole, and a dicyclopentadiene/cyclopentadiene/methylcyclopentadiene content of 40-80 wt % (see, WO2013/176712 of Block).

Escorez® 5615 is a hydrocarbon polymer additive available from ExxonMobil Chemical Company. It has a softening point of 118° C., a weight average molecular weight of about 500 g/mole, and a dicyclopentadiene/cyclopentadiene/methylcyclopentadiene content of 40-80 wt % (see, WO2013/176712 of Block).

Hydrogels

Hydrogels are 3-dimensional, cross-linked networks of water-soluble polymers. The porous structure of hydrogels can be altered by changing the density of cross-linking. The degree of cross-linking can alter the rate of loading a drug, and it can alter the rate of drug release. The present disclosure can encompass a hydrogel that consists of one of the following polymers or alternatively, that comprises one or more of the following polymers (e.g., as a block polymer). The polymers include, poly(ethylene oxide) (PEO), poly (propylene oxide) (PPO), poly(lactide-co-glycolic acid) (PLGA), poly(N-isopropylacrylamide) (PNIPAM), poly (propylene fumarate) (PPF), poly(caprolactone) (PCL), poly (urethane) (PU), and poly(organophosphazene) (POP). An example of a block polymer is PEO-PPO-PEO. In exclusionary embodiments, the present disclosure can exclude a hydrogel that includes PEO, PPO, PLGA, PNIPAM, PPF, PCL, PU or POP. The present disclosure also encompasses hydrogels that contain a cyclodextrin, where the cyclodextrin is cross-linked to hydrogel (see, Hoare et al (2008) Hydrogels in drug delivery: Progress and challenges. Polymer. 49:1993-2007). Hydrogels of the present disclosure can be ethylene vinylacetate, alginic acid, gums, polyvinylalcohol hydrogel; silicone hydrogel; polyvinylalcohol/dextran hydrogel; alginate hydrogel; alginate-pyrrole hydrogel; gelatin/chitosan hydrogel; polyacrylic acid hydrogel; photo crosslinked polyacrylic acid hydrogel; amidated pectin hydrogel; pectin hydrogel; gelatin hydrogel; polyethylene glycol (PEG) hydrogel; carboxymethylcellulose/gelatin hydrogel; chitosan hydrogel, as well as mixtures thereof, or copolymers thereof, and the like. Hydrogel with crosslinks are available (Lee et al (2003) Eur. J. Pharm. Biopharm. 56:407-412.

Printing Active Ingredients and Excipients on Dried Hydrogels

Dried hydrogel can take the form of a "xerogel" or of a film. Xerogel can be made by freeze drying a hydrogel. Film can be made by evaporative drying or casting from organic solutions. Spotting device can be used to apply microdrops in predetermined locations of dried hydrogel or on a film (see, e.g., U.S. Pat. No. 6,642,054 of Schermer). Where dried hydrogel or film takes the form of a layer, microdrops can be applied to one side only or to both sides. Where more than one type of drug is to be applied and where at least two of the drugs are incompatible with each other, or where a drug an excipient are to be applied, and where these are incompatible with each other, these can be applied at different locations on the dried hydrogel or on the film. (Drop size of microdrops can be, e.g., 0.05 nanoliters (nL)-10,000 nL, 0.5 nL-200 nL, 10 nL-100 nL, and so on. Drug, active ingredient, and/or excipient is not incorporated into the dried hydrogel, but is instead printed on its surface or surfaces. Printing on dried hydrogel avoids problems arising from incompatibility of drug, active ingredient, and/or excipient with the hydrogel itself. See, US 2008/0095848 of Stabenau, which is incorporated by reference in its entirety.

Cyclodextrins

Cyclodextrins are cyclic oligosaccharides of (alpha-1,4)-linked alpha-D-glucopyranose units, with a lipophilic central cavity and a hydrophilic outer surface. As a result of their molecular structure and shape, they can act as molecular containers by trapping drugs or other molecules in their internal cavity. No covalent bonds are formed or broken during drug cyclodextrin complex formation, and in aqueous solution, the complexes readily dissociate and free drug molecules remain in equilibrium with the molecules bound within the cyclodextrin cavity (see, Tiwari et al (2010) Cyclodextrins in delivery systems: Applications. J. Pharm.

Bioallied Sci. 2:72-79). Derivatives of cyclodextrins that are hydroxypropyl (HP), methyl (M) and sulfobutylether (SBE) substituents are useful as pharmaceutical excipients.

Cyclodextrins for use, for example, in cannabinoid/cyclodextrin complex, include beta-cyclodextrins such as hydroxypropyl-beta-cyclodextrin, sulfobutylether-beta-cyclodextrin, maltoxyl-beta-cyclodextrin, and methylated cyclodextrins. Encompassed are alpha-cyclodextrins (6 glucopyranose units), beta-cyclodextrins (7 glucopyranose units), and gamma-cyclodextrins (8 glucopyranose units). Methylated cyclodextrins can improve acqueous solubility, dissolution rate, and bioavailability of cannabinoids.

The present disclosure provides a dermal patch (or buccal patch) comprising a dextrin where the dextrin is not complexed with a pharmaceutical agent, and a dermal patch (or buccal patch) comprising a dextrin where the dextrin is, in fact, complexed with a pharmaceutical agent.

In exclusionary embodiments, the present disclosure can exclude a formulation that comprises a cyclodextrin, or that comprises an alpha-cyclodextrin, or that comprises a beta-cyclodextrin, or that comprises a gamma-cyclodextrin. What can also be excluded is a device that comprises a cyclodextrin, such as an adhesive dermal patch comprising a dextrin or a buccal patch comprising a dextrin.

Apertures and Pores

The present disclosure can encompass films, sheets, layers, membranes, and the like, including those with a plurality of apertures or pores. In some aspects, the apertures or pores have an average diameter of 20 nm, 40 nm, 50 nm, 100 nm, 200 nm, 300 nm, 400 nm, 500 nm, 600 nm, 800 nm, 0.001 mm, 0.002, 0.005 mm, 0.010 mm, 0.015 mm, 0.020 mm, 0.025 mm, 0.030 mm, 0.040 mm, 0.050 mm, 0.075 mm, 0.10 mm, 0.20 mm, 0.30 mm, 0.40 mm. 0.50 mm, and the like. Also, the pores can have a diameter range where the range is bracketed by any two of these values. In other aspects, the apertures or pores have a diameter in the range of 20-40 nm, 40-60 nm, 60-80 nm, 50-100 nm, 100-200 nm, 200-400 nm, 400-600 nm, 600-800 nm, 800-1,000 nm, 0.001-0.002 mm, 0.001-0.005 mm, 0.005-0.010 mm, 0.010-0.020 mm, 0.020-0.040 mm, 0.025-0.050 mm, 0.050-0.075 mm, 0.075-0.10 mm, 0.10-0.20 mm, 0.20 mm-0.40 mm, 0.25-0.50 mm, 0.50-0.75 mm, 0.50-1.00 mm, 0.1-0.2 mm, and so on. In exclusionary embodiments, the present disclosure can exclude films, sheets, layers, and the like, that have apertures or pores having any of the above average values, or that are deseribabie by any of the above ranges.

Porous membranes can take the form of hydrophilic porous membranes and hydrophobic porous membranes, without implying any limitation. Hydrophobic membranes, such as hydrophobic polyethylene (PE) membranes, can be made more hydrophilic by alcohol or surfactants (see, WO2010/072233 of Calis). Pores in membranes of the present disclosure can have an average diameter of about 5 micrometers, about 10, about 15, about 20, about 25, about 30, about 40, about 50, about 60, about 70, about 80, about 90, about 100, about 110, about 120, about 130, about 140, about 150, about 160, about 170, about 180, about 190, or about 200 micrometers, and the like. Also, pores in the membranes can have an average diameter somewhere in the range 5-20 micrometers, 20-40 micrometers, 40-60 micrometers, 60-80 micrometers, 80-100 micrometers, 100-120 micrometers, 120-140 micrometers, 140-160 micrometers, 160-180 micrometers, 180-200 micrometers, and so on. In exclusionary embodiments, the present disclosure can exclude any membrane that is characterized by one of the above "about" values or that is characterizable by one of the above ranges.

For any given film, sheet, or layer, and the like, the area of a plurality of apertures or the area of a plurality of pores can occupy about 1%, about 2%, about 4%, about 6%, about 8%, about 10%, about 15%, about 20%, about 25%, about 30%, about 35%, about 40%, about 45%, about 50%, about 55%, about 60%, about 65%, about 70%, about 75%, about 80%, about 85%, about 90%, and the like of the surface area. In exclusionary embodiments, the present disclosure can exclude any film, sheet, or layer, where the area does not occupy one or more of the given percentage values, or where the area does not occupy a range between any two of the above given percentage values. The above parameters also can apply to a film, sheet, or layer, with perforations, where the value of the area for the perforation is measured flush with a surface of the film, sheet, or layer.

Solubilizers and Surfactants

Solubilizers such as detergents, surfactants, organic solvents, and chaotropic agents, are available for the present disclosure. These can be one or more of, polyethylene glycol (PEG), propylene glycol, dibutyl subacetate, glycerol, diethyl, phthalate (phthalate esters), triacetin, citrate esters-triethyl citrate, acetyltriethyl citrate, tributyl citrate, acetyltributyl citrate, benzyl benzoate, sorbitol, xylitol, bis(2-ethyllhexyl) adipate, mineral oil, polyhydric alcohols such as glycerin and sorbitol, glycerol esters such as glycerol, triacetate; fatty acid triglycerides, polyoxyethylene sorbitan, fatty acid esters such as TWEENS, polyoxyethylene mono-alkyl ethers such as BRIJ series and MYRJ series, sucrose monoesters, lanolin esters, lanolin ethers. These are available from Sigma-Aldrich, St. Louis, Mo. In exclusionary embodiments, what can be excluded is any composition, formulation, dermal patch, and methods that comprise one or more of these solubilizers or surfactants.

The present disclosure can encompass compositions, formulations, devices, and methods, that comprise one or more surfactants, such as, sorbitan trioleate, sorbitan mono-oleate, sorbitan monolaurate, polyoxyethylene (20) sorbitan monolaurate, polyoxyethylene (20) sorbitan monooleate, oleyl polyoxytheylene (2) ether, stearyl polyoxyethylene (2) ether, lauryl polyoxyethylene (4) ether, block copolymers of oxyethylene and oxypropylene, diethylene glycol dioleate, tetrahydrofurfuryl oleate, ethyl oleate, isopropyl myristate, isopropyl palmitate, glyceryl monooleate, glyceryl monostearate, glyceryl monoricinoleate, cetyl alcohol, stearyl alcohol, cetyl pyridinium chloride, olive oil, glyceryl, monolaurate, corn oil, cotton seed oil, and sunflower seed oil. In exclusionary embodiments, the present disclosure can exclude one or more of the above chemicals, and can also exclude a composition, formulations, device, and method that comprises any of the above chemicals.

Franz Diffusion Cell Method

Transdermal flux of cannabinoids can be measured In Vitro through human cadaver epidermis using Franz Diffusion Cell Method. Samples of 300 microliters can be taken of the receiving solution and analyzed by HPLC for amount ofcannabinoid substance that passed through the epidermis.

Monolithic Patches

The following writing is from US 2017/0071870 (Ser. No. 15/265,823) of Weimann, which is incorporated herein by reference in its entirety.

Transdermal monolithic CBD patch formulation: Adhesive polymer: 60-95, CBD: 5-20 Penetration enhancer: 0-20, Adhesive polymer: Acrylate from Hankel, Silicone from Dow Corning. PIB from BASF CBD: pure crystalline powder Penetration enhancer: Oleic acid, isopropyl palmitate (IPP), dimethylsulfoxide (DMSO), 1,2-propylene glycol (1.2-PG), isopropylmyristate (IPM). In this example, the dry adhesive matrix is 30-50 micrometers thick. The area of the patch can be square or oval. The best size of the patch is 20 cm$^2$ by 40 cm$^2$.

In a monolithic design, a release liner is coated with a mixture of CBD and a PIB or amine-compaible silicone skin adhesive laminated to the backing material. How the Monolithic CBD Patch Works: Step 1. CBD is dissolved in ethyl alcohol or 1,2 PG and mixed into the adhesive solution and penetration enhancer is added if needed. Step 2. Adhesive mix is dispensed on the release liner by means of "knife-over-roll" coating method and dried in the oven at drying time from 1 min to 3 min or until all residual solvents are below 1 ppm. Step 3. Dried adhesive film is laminated to the backing film by means of nipping and edges are slit for farther die cutting of the patches. Step 4. The laminate is placed on the die cutting machine and proper size patches are cut and later packaged in the pouches and boxes.

Formulations of monolithic patches are prepared by solubilizing CBD in different adhesives and CBD transdermal flux is performed through human cadaver skin using Franz Diffusion Cell method. High transdermal flux of CBD occurs from a formulation that comprises PIB adhesive and 10% CBD. This high transdermal CBD flux shows that a patch measuring 20 cm$^2$ can deliver a daily systemic dose of about 5 mg of CBD.

Exemplary Monolithic Patch Invention Formulations: Formulation 1. 10% CBD in EtOH. Formulation 2. 10% CBD in EtOH/H$_2$O (9/1). Formulation 3. Penetration enhancers: 1,2PG, IPP, oleic acid, DMSO.

In a first monolithic-style device, a skin adhesive is mixed with the CBD to define a monolithic mixture of adhesive and CBD. The skin adhesive is coated on a backing that is preferably occlusive. The skin adhesive is preferably an amine-compatible silicone adhesive.

In a second monolithic-style device, a skin adhesive is mixed with the CBD (which may be present as substantially pure CBD or an oil extract of a cannabis plant which comprises CBD and other cannabinoids) to define a substantially monolithic mixture of adhesive and CBD. The skin adhesive is preferably a polyisobutylene adhesive having a viscosity-average molecular weight ranging from about 30,000 Daltons to about 70,000 Daltons, preferably, from about 35,000 Daltons to about 65,000 Daltons, and more preferably from about 40,000 Daltons to about 60,000 Daltons.

Manufacturing Method for Monolithic Patch

In methods of manufacturing embodiments, monolithic patch can be made as follows. Cannabis oil or one or more pure cannabinoids can be combined with permeation enhancer only, combined with carrier only, or combined with both permeation enhancer and carrier. Carrier can comprise, for example, one or more of oleic acid and dodecylmethyl sulfoxide. Then one or more pure terpenes, or on essential oil, or a combination of an essential oil and one or more pure terpenes, is mixed with the above combination. Then, a polymer such as a silicone polymer is mixed in. Finally, the mixture is spread into one or more sheets, cured at room temperature for several hours or longer. After drying, a foam backing layer is applied, and then the product is cut into shapes (e.g., squares, rectangles, ovals, round-edged squares or round-edged rectangles, circles) suitable for applying to the skin of a person.

CBD is dissolved in ethyl alcohol or 1,2-propylene glycol (1,2 PG) and mixed into the adhesive solution and penetration enhancer is added if needed. Adhesive mix is dispensed on the release liner by means of "knife-over-roll" coating method and dried in the oven at drying time from 1 min to 3 min or until all residual solvents are below 1 ppm. Dried adhesive film is laminated to the backing film by means of nipping and edges are slit for further die cutting of the patches. The laminate is placed on the die cutting machine and proper size patches are cut and later packaged in the pouches and boxes.

Monolithic device may also include one or more penetration enhancers, including oleic acid, isopropyl palmitate (IPP), DMSO, 1,2 propylene glycol, and isopropyl myristate (IPM). The amount of penetration enhancer preferably ranges from zero to about ten (10) percent by weight of the matrix. In an exclusionary embodiment, the present disclosure can exclude any patch or any formulation that has more than one type of penetration enhancer, or more than two types of penetration enhancers, and the like.

The skin contact area of device is preferably at least about 10 cm$^2$, more preferably at least about 15 cm$^2$, and still more preferably at least about 1.8 cm$^2$. At the same time, the skin contact area of device is preferably no more than about 30 cm$^2$, preferably no more than about 25 cm$^2$, and still more preferably no more than about 22 cm$^2$. At a given flux rate, the skin contact area may be selected to achieve the desired daily dose of CBD (or the dose over whatever time period is of therapeutic interest). The above writing is from US 2017/0071870 (Ser. No. 15/265,823) of Weimann.

Knife-Over-Roll Coating

Knife coating is a process by which a thin liquid coating is formed on a continuous web by the application of an excess of coating liquid which is subsequently metered by a rigid knife held in close proximity to a rigidly supported web. The thickness of the coating depends primarily on the clearance, or gap, between the knife and the web, and upon the geometry of the gap (bevel angle, length). Roll coating is a process by which a thin liquid film is formed on a continuous web by use of two or more rotating rolls, such that the fluid flow in a small gap between a pair of rotating rolls is the primary factor controlling the thickness and uniformity of the coated film. The thickness of the coating depends primarily on the gap between adjacent rolls and their relative speeds. Two basic types of roll coaters are distinguished by the relative direction of roll surface motion in the gap: in forward roll coating the roll surfaces move in the same direction and in reverse roll coating they move in opposite directions. In terms of the flow fields, knife coating is a subset of forward roll coating where one surface is stationary. See, Coyle, D. J (1997) Knife and Roll Coating in Liquid Film Coating (ed. S. F. Kistler and P. M. Schweizer). Chapman & Hall, London; W. Rehnby, M. Gustafsson, M. Skrifvars (June 2008) Conference Paper, Coating of Textile Fabrics with Conductive Polymers for Smart Textile Applications, pages 100-103.

Suitable examples of such amine-compatibie silicone adhesives include the BiO-PSA 7-4301 and 7-4302 skin adhesives supplied by Dow Corning. BIO-PSA 7-4301 is a high tack, amine-compatible silicone adhesive in heptane available with a solids content of 60 percent and 70 percent and corresponding viscosities at 20.degree. C. of 450 mPa-s and 1600 mPa-s. BIO-PSA 7-4302 is a high tack, amine-compatibie silicone adhesive in ethyl acetate with a solids content of 60 percent by weight and a viscosity of 1200 mPa-s at 20 degrees C. The skin adhesive 30 is coated to a thickness per unit area on the membrane that is preferably from about 10 to about 20 g/m$^2$, more preferably from about 12-18 g/m$^2$, and still more preferably from about 14-16 g/m$^2$.

Reservoir Patches

In embodiments, what is provided is a device comprising a reservoir in the shape of a "ravioli" constructed with microporous hydrophilic or hydrophobic membrane on one side and occlusive film on other side.

In embodiments, device comprises transdermal reservoir patch formulation as thixotropic alcohol or alcohol/water solution gelled with hydroxyalkyl cellulose containing CBD at high concentration ranging from 1% to 50% CBD Moreover, device comprises transdermal reservoir patch formulation comprising a reservoir containing thixotropic alcohol or alcohol/water solution gelled with hydroxyalkyl cellulose and containing CBD at a high concentration, ranging from 1% to 50% and skin penetration enhancers in a concentration range of 0% to 10%.

What is also encompassed, is transdermal patch formulation comprising a reservoir in shape of "ravioli" constructed with microporous hydrophilic or hydrophobic membrane on one side and occlusive film on other side where the microporous membrane is coated with thin layer of silicone adhesive. In delivery embodiments, reservoir patch of 20 cm$^2$ is capable of systemically delivering CBD at about 0.5 mg/day, about 1.0 mg/day, about 1.5 mg/day, about 2.0 mg/day, about 5.0 mg/day, about 10 mg/day, about 15 mg/day, about 20 mg/day, about 25 mg/day, about 30 mg/day, about 35 mg/day, about 40 mg/day, and the like.

In other delivery embodiments, reservoir patch of 20 cm$^2$ is capable of systemically delivering CBD at least 0.5 mg/day, at least 1.0 mg/day, at least 1.5 mg/day, at least 2.0 mg/day, at least 5.0 mg/day, at least 10 mg/day, at least 15 mg/day, at least 20 mg/day, about 25 mg/day, about 30 mg/day, at least 35 mg/day, at least 40 mg/day, and so on.

Dimple-style Reservoir vs. Balloon-Style Reservoir for Reservoir Patch Device

In a balloon embodiment, the present disclose can include a reservoir that is conformed like a sealed bag (or like a continual bag) or like a sealed balloon. In this embodiment, the reservoir is made of a material that is separate from backing and separate from permeable layer. In this embodiment, the reservoir may or may not be attached to backing or permeable layer by way of an adhesive or heat seal.

In a dimple embodiment, the reservoir has on a distal side a backing that has a dimple (or outpouching) where the dimple is conformed to hold drug, and where the reservoir has on proximal side a permeable layer. Ih other words, what prevents drug from spillout out of the outpouching is this permeable layer.

The backing and permeable layer are attached to each other, to prevent leaking of the drug. Attachment can be via an adhesive or heat-sealing. The present disclosure can exclude devices where this attachment is by adhesive, and can exclude devices where this attachment is by heat-sealing. The present disclose can exclude devices with balloon reservoir. In other embodiments, the present disclosure can exclude devices with a dimple reservoir.

In the dimple embodiment, the permeable layer can comprise a plurality of slits, a plurality of tiny holes, or by being made of a porous layer. The present disclosure can exclude device with dimple reservoir.

Dimple reservoir device can include (or exclude) a layer that that resides in between drug and permeable layer. Also, dimple reservoir device can include (or exclude) a layer that resides on side of permeable layer facing the skin, where this layer is in substantial contact with the permeable layer. This layer that is on side of permeable layer of skin can be distal to adhesive layer and peel able backing layer.

Permeable layer can comprise permeable polypropylene film (US 2006/0024520; US 20016/115585), permeable polyethylene film (U.S. Pat. No. 4,793,003: WO 2006/070672); permeable polyurethane film (U.S. Pat. No. 9,566,423).

Shapes of Reservoirs That After Delivery Rate Over the Course of Time

Reservoir of the present disclosure can be manufactured in predetermine shape, so that rate of release of an active agent to the skin or to a mucosal surface various over the course of hours, during the time frame when patch device is worn by a patient. For example, reservoir can be conical, where the wide surface (base of cone) is situated at the distal portion of patch device and where point of the cone is situated at the proximal portion of patch device. Proximal means the side of patch device closest to the skin, distal means the side of patch device farthest away from the skin. With cone reservoir, rate of drug transfer from patch to skin or mucosal surface gradually decreases over time. Reservoir can be hemispherical, resembling a gum drop, with base of gum drop closest to proximal side of patch device, and rounded surface of gum drop closest to distal side of patch device. Hemispherical reservoir gives initial rapid rate of drug release followed by rapid decrease in rate of drug release. Reservoir can also have edges that are perpendicular to the skin-facing portion of the patch, that is, perpendicular to the peelable release of the dermal patch (in the event that the patch has a peelable release). See, U.S. Pat. No. 6,207,181 of Herrman, which is incorporated herein by reference in its entirety. The present disclosure can exclude a device with conical reservoir, with hemispherical reservoir, and/or hemispherical reservoir.

The reservoir device of the present disclosure can have only one conical reservoir, only two conical reservoirs, only three conical reservoir, at least one conical reservoir, at least two conical reservoirs, at least three conical reservoirs. The reservoir device can have only one, only two, only three, at least one, at least two, at least three hemispherical reservoirs. The reservoir device can have only one, only two, only three, at least one, at least, two, at least three perpendicular sided reservoirs. Moreover, the reservoir device can have only conical reservoir(s), only hemispherical reservoir(s), only parallel sided reservoir(s), a combination of only conical reservoir(s) and hemispherical reservoir(s), a combination of only conical reservoir(s) and parallel side reservoir(s), a combination of only hemispherical and parallel side reservoir(s), or a combination of all three of conical, parallel side, and hemispherical reservoirs. The present disclosure also provides reservoirs of an ambiguo shape, such as that resembling a wrinkled, partially filled balloon, either alone or in combination with a conical, hemispherical, and/or parallel shaped reservoir. The present disclosure also provides reservoirs having the shape of a hot dog, either alone or in combination with a conical, hemispherical, and/or parallel shaped reservoir.

Porous Membranes

Hydrophilic, porous membrane preferably has a mean flow pore size of no more than about 1 micrometer, preferably not more than about 0.8 micrometers, still more preferably no more than about 0.4 microns, and even more preferably no more than about 0.2 micrometers. At the same time, porous membrane preferably has a mean flow pore size of no less than about 0.02 micrometers, more preferably no less than about 0.04 microns, still more preferably no less than about 0.06 microns, and even more preferably no less than about 0.08 micrometers. The mean flow pore size may be determined in accordance with the method set forth at page 17, line 22 to page 18, line 4 of published PCT Application WO 2010072233, the entirety of which is hereby incorporated by reference.

In the same or other examples, hydrophilic porous membrane preferably has a porosity of at least about 60 percent, more preferably at least about 65 percent, and still more preferably at least about 70 percent. At the same time, hydrophilic porous membrane preferably has a porosity of no more than about 90 percent, more preferably no more than about 85 percent, and still more preferably no more than about 80 percent. Porosity values may be calculated as described at page 7, lines 24 to 27 of WO 2010072233.

In the same or other examples, hydrophilic porous membrane preferably has a thickness of no more than about 50 micrometers, preferably no more than about 40 micrometers, and even more preferably no more than about 35 micrometers. At the same time, hydrophilic porous membrane preferably has a thickness of no less than about 10 micrometers, more preferably no less than about 20 micrometer, and still more preferably no less than about 25 micrometers. Membrane thicknesses may be determined as described at page 18, lines 19-21 of WO 2010072233.

In the same or other examples, hydrophilic porous membrane preferably has an air permeability as determined by the Gurley Test Method (according to ISO 5636-5) that is preferably at least about 10 sec/50 ml, more preferably at least about 20 sec/50 ml, and still more preferably at least about 25 sec/50 ml. At the same time, hydrophilic porous membrane preferably has an air permeability of no more than about 50 sec/50 ml, more preferably no more than about 40 sec/50 ml, and still more preferably no more than about 35 sec/50 ml.

In the same or other examples, hydrophilic porous membrane preferably has a tensile strength in the machine direction as determined by ASTM D882-12 that is preferably at least about 10 MPa, more preferably at least about 15 MPa, and still more preferably at least about 20 MPa. In the same or other examples, the hydrophilic porous membrane preferably has a percent elongation in the machine direction as determined by ASTM D882-12 that is preferably at least about 10 percent, more preferably at least about 15 percent, and still more preferably at least about 20 percent.

Hydrophilic porous membrane preferably comprises at least one polymeric material. In one example, hydrophilic porous membrane comprises a polyolefin polymer and a hydrophilic component that comprises a hydrophilic polymer and optionally, a surfactant. As used herein, the term "hydrophilic" when used to describe a porous membrane refers to a membrane that at 20 degrees C. provides a water flux for demineralized water through the membrane of at least 0.5 liters/($m^2$ hours bar).

The content of the polyolefin polymer is preferably less than or equal to 98 percent by weight based on the total dry weight of the membrane, and the content of the hydrophilic component(s) is preferably at least 2 weight percent based on the total dry weight of the membrane. In certain preferred examples, the membrane is formed by combining the polyolefin polymer with the hydrophilic components(s) and optional additives with a solvent to form a blend in the form of a gel, a solution, or a homogeneous mixture, followed by extruding the blend. Suitable polyolelins (such as polyethylene), hydrophilic components, and additives are described in WO 2010072233.

Adhesives and Tackifiers

Bioadhesive polymer of the present disclosure, when swollen, creates a flexible network through with drug can diffuse. Bioadhesive material serves a matrix for retaining pharmaceutical agents, until patch is applied to the skin or to a mucosal surface of the consumer. Bioadhesive materials include, hydroxypropyl cellulose, carbopol, poly(vinyl pyrrolidone), sodium carboxymethyl cellulose, hydroxyethyl cellulose, polycarbophil, pectin, chitosan, xanthan gum, locust bean gum, hydroxypropyl methylcellulose, poly(vinyl alcohol), poly(isoprene), poly(isobutylene) (see, Shojaei et al (June 2001) Systemic drug delivery via the buccal mucosal route. Pharmaceutical Technology. Pages 70-81).

Chemistry of Acrylic Adhesives and Chemistry of Tackifiers of the Present Disclosure Duro-Tak® 87-2516 is an acrylic copolymer adhesive containing EHA, vinylacetate, and hydroxyethylacrylate. EHA is 2-ethylhexylacrylate (see, U.S. Pat. No. 5,783,208 of Venkateshwaran). Duro-Tak® 87-2516 is an acrylate-vinylacetate copolymer with a hydroxyl group (see, Zhao, Park, Kim, Lee (2002) Drug Devel. Industrial Pharmacol. 28:1125-1131). Duro-Tak® 87-2516 has viscosity of 4350 cp at 41.5% solids (see, US2006/173,124 of Paul), Duro-Tak® 87-2516 is hydroxyfunctional and crosslinked (see, US 2002/0058068 of Houze). Duro-Tak® 87-2516 is an acrylate-vinyl acetate self-curing pressure-sensitive adhesive in an organic solvent (see, US 2006/0121102 of Chiang).

Duro-Tak® 87-4287 is a copolymer with 2-ethylhexyl acrylate as the main repeating monomer unit. Duro-Tak 87-4287 is a copolymer with vinyl acetate and contains OH— functional groups as 2-hydroxyethyl acrylate is also part of the polymer composition (Wolff (2014) Pharm. Res. 31:2186-2202).

Duro-Tak® 87-2287 is a polyacrylate adhesive. According to U.S. Pat. No. 5,693,335 of Xia, "Duro-Tak 87-2287 is a solution polyacrylate adhesive available from National Starch and Chemical Co. Its monomer composition is: vinyl acetate, 28%; 2-ethylhexyl acrylate, 67%; hydroxyethyl acrylate, 4.9% glycidal methacrylate, 0.1%. It contains no crosslinking agent. It is available as a 50% solids solution in ethyl acetate." See also, U.S. Pat. No. 6,071,531 of Jona. According to U.S. Pat. No. 5,780,050 of Jain. Duro-Tak® 87-2287 is an acrylic adhesive free of acid functional groups. According to US 2009/0258061 of Hwang, "Duro-Tak® 87-2287 is an adhesive is derived from a monomer composition of vinyl acetate, 28%; 2-ethylhexyl acrylate, 67%; hydroxyethyl acrylate, 4.9%; and glycidyl methacrylate, 0.1%, see U.S. Pat. No. 5,693,335."

DuroTak® 87-900A is an acrylic pressure-sensitive adhesive that comprises 2-ethylhexyl acrylate, butyl acetate, t-octyl acrylamide, and methyl methacrylate. This list of chemicals was accepted, as a substitute for "DuroTak® 87-900A" by the patent examiner in file history of US 2009/0297590 of Yamagi. According to a Product Selection Guide, DuroTak® 87-900A has no crosslinker, no vinyl acetate, 43% solids, viscosity of 1800 cP (see, DURO-TAK and GELVA Transdermal Pressure Sensitive Adhesives. Product Selection Guide (2013) Hehkel Corp., Bridgewater, N.J. (2 pages)). According to Wolff (2014) Pharm. Res. 31:2186-2202, Dura-Tak 87-900A is, "Duro-Tak 87-900A . . . have 2-ethylhexylacrylate as the main repeating monomer unit . . . Duro-Tak 87-900A contains besides 2-ethylhexylacrylate, butylacrylate, methyl methacrylate and tertiary-octyl acrylamide units." See also, para. 0031 of Yamagi US 2009/0297590. Duro-Tak 87-900A contains 2-ethylhexyl acrylate as the main repeating monomer unit, and also contains butylacrylate, methyl methacrylate and tertiary-octyl acrylamide units (Wolff (2014) Pharm. Res. 31:2186-2202).

Duro-Tak® 87-2510 has been described as, "copolymer: acrylate; functional group: OH; 40.5% solution of noncrosslinking acrylic copolymer, 4500 cps, solubility parameter 16." (see, Kim, Gwak, Chun (2014) Arch. Pharm. Res. 27:763-768).

Escorez® 5400 is described as, "dicyclopentadiene (DCPD) resin" (see, U.S. Pat. No. 9,296,930 of Hu); "hydrogenated polycyclopentadiene resin" (see, U.S. Pat. No. 9,039,862 of Lotz); a "hydrocarbon tackifying resin, having a molecular weight of about 400 grams/mole, a softening point of 103 degrees C., and a glass transition temperature of about 50 degrees C." (see, U.S. Pat. No. 9,074,087 of Chen); a "cycloalphiphatic hydrocarbon tackifying resin having a ring and ball softening point from about 100 degrees C. to about 106 degrees C." (see, U.S. Pat. No. 9,803,113 of Tse).

Escorez® 5400 has the following characteristics: softening point 218.1 degrees F., initial color: 0.6 YI; thermal color stability: 5 hours, 347 degrees F. (175 degrees C.) 6.4 YI, melt viscosity: 320 degrees F. (160 degrees C. of 800 cP; molecular weight (number average; Mn) 400 g/mol; molecular weight (Mw) 670 g/mol: glass transition temperature (Tg): 126 degrees F. (Product Datasheet, ExxonMobil, Escorez® 5400 Tackifying Resin).

Permeation Enhancers

The present disclosure provides permeation enhancers, for example, for use with a dermal patch or for a buccal patch. Suitable permeation enhancers include, 23-lauryl ether, Aprotinin, Azone, Benzalkonium chloride, Cetylpyridinium chloride, Cetyltrimethylammonium bromide, Cyclodextrin, Dextran sulfate, Lauric acid, Lauric acid/propylene glycol, Lysophosphatidylcholine, Menthol, Methoxysalicylate, Methyl oleate, Oleic acid, Phosphatidylcholine, Polyoxyethylene, Polysorbate 80, Sodium EDTA, Sodium glycocholate, Sodium glycodeoxycholate, Sodium lauryl sulfate, Sodium salicylate, Sodium taurocholate, Sodium taurodeoxycholate, Sulfoxides, and Alkyl glycosides (see, Shojaei et al (June 2001) Systemic drug delivery via the buccal mucosal route. Pharmaceutical Technology. Pages 70-81). Other enhancers of the present disclosure are 1-octanol, 2-ethylhexanol, 1-nonanol, 1-decanol, and so on. In exclusionary embodiments, the present disclosure can exclude any formulation, composition, dermal patch, medical device, and such that comprises one or more of these permeation enhancers.

Permation enhancers of the present disclosure can be a biphasic composition having a lipid phase and a water phase. Lipid phase can be prepared by mixing isopropyl palmitate and lecithin. Water phase can be mixture of water and a surfactant. Surfactant can be Pluronic®, Pemulen®, Noveon®, or Carbopol®. Pemulen polymeric emulsifiers are high molecular weight, copolymers of acrylic acid and C10-C30 alkyl acrylate crosslinked with allyl pentaerythritol (Lubrizol, Inc. product sheet). Carbopol homopolymers are acrylic acid crosslinked with allyl sucrose or allyl pentaerythritol. Carbopol copolymer are acrylic acid and C10-C30 alkyl acrylate crosslinked with allyl pentaerythritol (Lubrizol, Inc. product sheet). Noveon® Polycarbophil, USP is a high molecular weight acrylic acid polymer crosslinked with divinyl glycol (Lubrizol, Inc. product sheet). Pluronic® polymers are block copolymers based on ethylene oxide and propylene oxide. They can junction as antifoaming agents, wetting agents, dispersants, thickeners, and emulsifiers (BASF, Inc. product sheet). The present disclosure can exclude any formulation, composition, device, method, and such, that comprise one or more of the molecules found in Pluronic®, Pemulen®, Noveon®, and Carbopol®.

PLOGel is "Pluronic Lecithin Organogel" (Pharmedica Enterprise, Selangor, Malaysia). PLOGel takes the form of an aqueous phase (240 mL poloxamer 407, potassium sorbate, water) and organic phase (60 mL lecithin, isopropyl palmitate, sorbic acid). The present disclosure can exclude any formulation, composition, device, method, and such that comprise one or more of PLOGel, poloxamer 407, potassium sorbate, isopropyl palmitate, sorbic acid, lecithin, and the like.

In exclusionary embodiments, the present disclosure can exclude any formulation, composition, device, method, and such that encompasses one of the above polymers, polymer compounds, and crosslinked polymer compositions.

Plurality of Layers

The present disclosure provides dermal patches, laminated sheets, and related methods that comprise a plurality of adhesive layers. In one embodiment, a monolithic patch has these layers, from most distal to most proximal: (1) Backing; (2) Adhesive; (3) Carrier layer containing active agent; (4) Contact adhesive, and (5) Protective liner. In an exclusionary embodiment, the present disclosure can exclude this embodiment.

In another embodiment that is characterized by having a "rate controlling layer," the monolithic patch has these layers, from distal to proximal: (1) Backing; (2) Adhesive; (3) Carrier layer containing active agent; (4) Adhesive layer; (5) Rate controlling polymer layer; (6) Adhesive layer; and (7) Protective liner. In an exclusionary embodiment, the present disclosure can exclude this embodiment.

The following concerns an embodiment where there is a "carrier layer" and where carrier layer is surrounded by and in contact with, on distal surface and on lateral surfaces, with an adhesive layer, and where carrier layer is surrounded by and in contact with, on proximal surface with "active ingredient permeable skin contact adhesive layer." More generally, speaking present disclosure encompasses a "hat embodiment" taking the form of a dermal patch or other medical device where a first layer has a distal surface, proximal surface, and lateral surfaces. In this "hat embodiment" the distal surface, proximal surface, and lateral surfaces, are all surrounded by and in contact with a "hat layer." The hat layer can be an adhesive layer or it can be an impermeable backing layer. The term "hat embodiment" and "hat layer" refer to the fact that the "hat layer" covers the first layer, in the same way that a man's hat covers the top of his head, as well as his ears, forehead, and back of his head. The present disclosure provides a device with these layers, from distal to proximal: (1) Backing; (2) Adhesive; (3) Carrier layer; (4) Active ingredient permeable skin contact adhesive; and (5) Protective liner. In this embodiment, the "hat" can cover the lateral sides of the carrier layer and also cover the lateral sides of the "active ingredient permeable skin contact adhesive layer." In an exclusionary embodiment, the present disclosure can exclude the above "hat" embodiment.

In another "hat" embodiment, the present disclosure provides, from distal to proximal: (1) Backing; (2) Adhesive layer; (3) Carrier layer; (4) Active ingredient permeable layer; (5) Rate-controlling polymer layer; and (6) Active ingredient permeable skin contact layer. The "hat" takes the form of backing plus adhesive layer, and had covers the laterals sides of all four of these layers: carrier layer, active ingredient permeable layer, rate-controlling polymer layer, and active ingredient permeable skin contact layer. In an exclusionary embodiment, the present disclosure can exclude the above "hat" embodiment.

In other exclusionary embodiments, the present disclosure can exclude devices where: (1) Carrier layer is in direct and substantial contact with backing layer; (2) Carrier layer is in direct and substantial contact with an adhesive layer; (3) Adhesive layer is in direct and substantial contact with rate-controlling polymer layer; (4) An adhesive layer is in direct and substantial contact with protective liner; (5) Where the device comprises a "hat" configuration of layers; (6) Carrier layer is in direct and substantial contact with active ingredient permeable layer, (7) Active ingredient permeable skin, contact layer is in direct and substantial contact with protective layer; (8) Active ingredient permeable skin contact layer is in direct and substantial contact with release liner or protective liner; (9) Where at least part of device has "hat" configuration and where only one layer is covered (surrounded on proximal face and on lateral faces) by the hat; (10) Where at least part of device has "hat" configuration and where only two layers are covered (surrounded on proximal face and on lateral faces) by the hat; (11) Where at least part of device has "hat" configuration and where only three layers are covered (surrounded on proximal face and on lateral faces) by the hat; (12) Where at least, part of device has "hat" configuration and where only four layers are covered (surrounded on proximal face and on lateral faces) by the hat. The exclusionary embodiments of the present disclosure encompass any combination of the above exclusions. The above may apply to reservoir patches where, optionally, "reservoir" takes the place of "carrier layer." Also, the above may apply to monolith patches.

Manufacturing Processes and Equipment

Sealing Two Strips Together at the Edges, and Coordinating Transverse Sealing to Create Pouches and Filling of the Pouches What is provided is a method to feed two strips into a machine with rollers to move the strips at the same speed, and to cause the two strips to move downwards, where the first face of the first strip is caused to contact the first lace of the second strip. The first face is caused to contact the first face of the second strip, in preparation for heating the edges of the two strips, thus sealing the two strips together, and in preparation for transverse heating, with heating at intervals of distance and time, thus creating a plurality of pockets in the sandwich of the two strips. When the two strips are moved downwards, the first strip and second strip are situated to form a thicker sandwich that moves downwards. Heaters resembling wheels or rollers, clamp down on the edges of the 2-strip sandwich, causing the 2-strip sandwich to form a long, closed tube. While the 2-strip sandwich moves downwards, what simultaneously occurs is simultaneous heating/sealing of a pair of transverse clamps. The transverse clamps create separate pouches in the long 2-strip sandwich. When the heated bars clamp down, what is created is a top seal of a previously-filled pouch, and the bottom seal of a pouch that has yet to be filled. Simultaneously occurring with heating/scaling at the edges by the heated wheels, and simultaneously occurring with heating by the transverse bars, is filling of each pouch as it is created, where filling is by a long tube that reaches down into the long sandwich to fill each pouch as it is created. See, U.S. Pat. No. 6,871,477 of Tucker, which is incorporated by reference in its entirety. The first strip can comprise an adhesive layer and permeable membrane, the second strip can be an impermeable backing, and the gel can comprise a cannabinoid in gel form.

Unrolling Three Different Layers From Rolls, Stripping Off Release Liners From Two of the Layers, Aligning the Three Layers Together to Form a Complex, and Rolling the Complex on to a Roll The present disclosure provides machinery that can unroll a plurality of rolls, optionally with stripping off a release-layer from one or more of the rolls, and taking up the stripped-off release-layer on an empty rotating drum or roll. For example, three different rolls can contain three different laminates, the first laminate comprising: (1) Protective backing; (2) Combined zone of transport enhancement and zone of containment; and (3) Release layer. The second laminate can comprise; (1) Adhesive layer; (2) Zone of transport control; and (3) Release liner. And the third laminate can comprise: (1) Support film; (2) Adhesive; and (3) Removable liner that is not removed during the above-mentioned method. Machinery can include three rolls on three rotating mechanisms of first, second, and third laminate, respectively. Machinery can include take-up rolls lor taking up release liners. Machinery can include a pair of rollers situated on opposite sides of moving sandwich of first laminate and second laminate for use in bringing the two laminates together. Also, machinery can include a pair of rollers situated on opposite side of the nascent 3-part sandwich, where the 3-part sandwich takes the form of the combined (in contact with each other) first and second laminate and the entering third laminate. The entering third laminate is simultaneously unrolled from its roll and then combined with the complex of first and second laminate. The final product is then moved, by way of pairs of rollers situated on opposite sides of the moving final product, and also moved by way of individual rollers, e.g., rollers called over roller, under roll, and over idler roller. The above-disclosed machinery can also include a device for sealing laminates together, a corona discharge for enhancing the sealing of the laminates together, a device for depositing a drug or adhesive or other composition on one or more of the laminates as the laminate is unrolled from its roll, and cutting devices for separating the sandwich of three laminates into patches. See, U.S. Pat. No. 5,370,924, which is incorporated herein by reference in its entirety.

Layered device may be assembled and then sealed by vacuum forming or by heat sealing without vacuum. In exclusionary embodiment, the present, disclosure can exclude machinery, methods, and patches, made using one or more of vacuum forming, heat sealing, corona discharge, one or more crimp rolls, or cooperating nip.

Providing a Platen with Bar-Like Regions Separated by Channels, and Using the Platen to Stamp a Laminate, and to Provide Pressure on Regions That Need to be Collapsed, While Refraining From Providing Pressure on Regions That Contain Drug and Matrix The present disclosure provides machinery, such as a platen with bar-like regions separated by channels, and where the bar-like regions are optionally heated. The platen can be used to selectively compress parts of a laminate, where the laminate (the "workpiece") comprises an upper layer that is a cellular region and a lower layer that is a skin adhesive. The platen selectively compresses the distal sides (the right edge and left edge), resulting in collapse of the distal sides of the laminate. Optionally, only the part of the laminate destined to be collapsed is provided with the adhesive. The cellular region can be reticulated or it can be non-reticulated. The cellular region can be made of foamed thermoplastic resin. Cell size can be about 0.05, about 0.1, about 0.2, about 0.4, about 0.6, about 0.80, about 1.0, about 1.2, about 1.4, about 1.6, about 1.8, about 2.0, about 2.5, about 3.0, or about 4.0 millimeters. Collapsed regions are such that drug cannot easily pass through collapsed regions. In embodiments, non-collapsed central area (the area that resided under the channel during platen-manufacturing process) can contain a distally-situated layer of drug-releasing matrix (which contains drug) in contact with a proximally-situated layer of a medium through which drug can diffuse. The layer of medium through which drug can diffuse can be, e.g., gel, cream, or ointment. "Distal" means away from the skin when patch is attached to skin, and "proximal" means on the side of patch that is closest to skin, when patch is attached to skin. The compressed lateral pans of patch may be called "straps." See, U.S. Pat. No. 5,505,958 of Bello, which is incorporated herein by reference in its entirety.

In exclusionary embodiments, the present disclosure can exclude patch devices with non-compressed cellular region, patch devices with compressed cellular region, layered structures with a distally-situated drug matrix and a proximally-situated gel, cream, ointment, or other medium through which drug can diffuse on its way to skin. Also, the present disclosure can exclude any composition, laminate, layered structure, and patch that was made via heating of a layered structure or via heating of a laminate.

Placing Drug Between Two Webs, Sealing Two Webs Together, Crimping the Sealed Webs to Form Pockets and Cutting the Sealed Web The present disclosure provides machinery and methods for using, as starting material, two different webs, each on a roller, where each web comprises one or more of a film, adhesive layers, impermeable layers, porous layers, and the like. The finished product takes the form of the two webs that are sealed together, and where an active ingredient, such as a composition comprising one or both cannabinoid and terpene, is contained therein. In the method, a first supply roll provides one web and a second supply roll provides second web. Machinery at various "stations" modify one of the webs or modify both of the webs, as the webs move along a conveyor belt. One station, which is optional, is a corona discharge station. The corona discharge modifies the surface chemistry of one or both of the webs, prior to marriage of the two webs together by operation of two crimp rolls. The corona discharge modifies the surface chemistry to improve adhesive properties of the first web and/or of the second web. Corona discharge is preferred where dissimilar materials (one material of first web, and other material of second web) are to be adhesively joined. Dissimilar materials can be, e.g., polyester polymer and ethylene acrylic acid polymer.

Another station is deposit station, which deposits active substance on one of the webs, as the web moves towards the crimp roll. Deposit station can include a reservoir that contains drug and tube leading from reservoir to location on web surface where drug is to be deposited. The deposit station preferably occurs after the corona station. Also, the deposit station and corona station preferably act on the same web, though optionally deposit station can operate on first web and corona station can operate on second web. The two webs are securely fastened together in a station taking the form of a first crimp roll and a second crimp roll. These rolls resemble gears, in that first crimp roll has projections and second crimp roll has depressions, which act meashingly in the manner of a "tongue-and-groove" to compress the two webs together and, at the same time, to stamp the joined webs into a pocket-like shape. The regions of the first crimp roll and second crimp roll that mesh together are called a "cooperating nip."

Finally, after the webs pass through the corona station, drug deposit station, and crimp rolls, the joined webs are cut by rotary die cutter, to create flexible packages or flexible patches suitable marketing. Motors can drive rollers. Also, motors can drive crimp rolls. See, U.S. Pat. No. 4,782,647 of Williams which is incorporated herein by reference.

Separating Cut Patches From a Strip of Non-Cut Patches, and Transferring Cut Patches to a Carrier This describes only one step in procedure for making adhesive patches, e.g., monolithic devices and reservoir devices. The procedure involves a cutter, transfer devices resembling wedges, and rollers. The rollers function to move a first web and a second web, in the manner of a conveyer belt. The first web takes the form of an auxiliary layer film on top, and then just under it, a drug-containing adhesive layer that sits on top of a carrier film. The first web, which has these three layers, is then later on supplemented by a process layer, where the result is a web consisting of four layers (process layer on top, then auxiliary layer film, then drug-containing adhesive layer, and on the bottom, carrier film). An earlier-occurring cutting process has cut the auxiliary layer film and the drug-containing adhesive layer into blocks. The first web is moved in one direction, e.g., to the left, and then with the help of the transfer devices resembling wedges, the squares are separated from the carrier film (the carrier film is then moved away to the right) and also separated from the combination of auxiliary layer film and process layer (which is moved upwards), where the squares end up residing on a carrier film. At this point the blocks are separated from each other, and any scrap that had been created with the cutting process is then discarded. This refers to the situation where cutting creates discrete blocks and creates scraps in between the blocks. The supporting film supports the blocks and moves away to the left. See, U.S. Pat. No. 6,059,913 of Asmussen, which is incorporated herein in its entirety.

Cutting Laminate to Create Fully Cut-Out Region and, Within it, a Partially Cut (Scored) Region Machinery, methods, and workpiece of the present disclosure comprises sheet of laminate, where shapes of the sheet (rectangles, ovals, circles) are cut fully through the laminate, and where the edges of the cut-out laminate is called, "periphery" (outer cut). Where the cut-out laminate is circular, the periphery is the same as the circumferential region. In addition to being cut at the periphery, the sheet is simultaneously cut during the cutting operation in a region within the periphery (inner cut). The inner cut has a smaller diameter than the outer cut. Also, the inner cut is to a shorter depth than the outer cut. In the case of a 3-layer laminate (release layer; pressure-sensitive adhesive, backing), the outer cut slices through all three layers, but the inner cut slices only partially through the top layer (the release layer). This partial cutting is more properly called, "scoring" rather than "cutting." The goal of this 2-distance cutting method is to score the release layer to facilitate easy removal of the liner by the user, and at the same time, to avoid leaking of adhesive from the patch during storage of the patch. Machinery for the 2-distance cutting method can take the form of a roller covered with cutting stampers (similar to cookie-cutters). Each cookie cutter stamps all the way through the laminate. Within each cookie cutter resides a second (smaller diameter) cookie cutter which is sized so that it only cuts partially through the top layer of the laminate (thus only scoring the top layer). In an alternative machinery, a first roller bears an array of only the larger diameter (and longer cutting distance) cookie cutters, while the second roller bears an array of the smaller diameter (and scoring distance)

cookie cutters. In operation, the two rollers operate simultaneously, and the cookie cutters on the first roller are aligned exactly with the cookie cutters on the second roller and, in operation the cutting (cutting through all layers) occurs simultaneously with scoring, for each patch. See, U.S. Pat. No. 5,656,285 of Sablotsky, which is incorporated by reference in its entirety, hi addition to the one cutting roller (or to the two cutting rollers), the machinery can have a pressure roller and a support roller, for use in driving the sheet of laminate. In exclusionary embodiments, the present disclosure can exclude an adhesive dermal patch that has a scored region, such as a scored release layer.

Efficient Separation of Punched Patches From Scrap Web

During manufacture of adhesive patches, patches are stamped out from, or cut from, a sheet consisting of various layers. These layers may include backing, matrix containing a drug, skin adhesive, and release layer. During cutting, some of the punched patches that have not yet been separated from scrap web may cling to the scrap web as the scrap web is pulled away from the sheet. Where this clinging is maintained as the scrap web is pulled away, the result will be undesirable discarding of the clinging punched patches along with the scrap web. This type of undesired clinging can be increased by flow of adhesive out of the edges of the punched patch, followed by flow of the adhesive to contact the scrap web. Efficient separation of punched patches can be accomplished by way of a probe or probes that contact the punched patch and shove the punched patch on to a horizontally moving conveyor belt as the scrap web is drawn upwards for eventual discard. The probe can take the form of a rotating roller where the roller is covered with blocks having the same shape and exactly the same dimensions (or dimensioned to be about 5% smaller, about 10% smaller, about 15% smaller, about 20 smaller, and the like, in area, as compared to the punched patch). The blocks can have a shape, as viewed from "above," that is square, rectangular, oval, round, etc., and to have a shape corresponding to the punched patch. Thus, as the roller rotates, each block presses down on a corresponding punched patch (as the punched patch continues to move on the conveyor belt) while the scrap web is simultaneously detached and drawn upwards by the rotation of the roller. An alternative to using a roller covered with block probes, is a roller covered with flexible bristles. As the roller rotates, the bristles press springfully down on the punched patches, the bristles remaining bent, causing the punched patches to separate from the scrap web. At the same time, the bristles pressing on the scrap web are greatly bent at first, but as the scrap web is pulled upwards, the bristles spring out to their full (un-bent) length. See, US 2017/0136648 of Grader, which is incorporated herein by reference in its entirety. In an exclusionary embodiment, the present disclosure can exclude manufacturing machinery and methods, comprising a roller with blocks or a roller with bristles, for use in preventing punched patches from adhering to the scrap web.

Time Period for Measuring Flux

In embodiments, flux of a chemical, with transfer from a dermal patch to human skin, can be measured where flux is allow to continue uninterrupted over a period of time that is, about ten minutes, about 20 minutes, about 30 minutes, about 40 minutes about 50 minutes, about 60 minutes, about 1 hour, about 1.5 hours, about 2 hours, about 3 hours, about 4 hours, about 5 hours, about 6 hours, about 7 hours, about 8 hours, about 9 hours, about 10 hours, and the like. In a preferred embodiment, cumulative flux over a designated time period is measured. In other embodiments, the period of time is ten minutes, 20 minutes, 30 minutes, 40 minutes 50 minutes, 60 minutes, 1 hour, 1.5 hours, 2 hours, 3 hours, 4 hours, 5 hours, 6 hours 7 hours, 8 hours, 9 hours, about 10 hours, and the like.

Flux is preferably measured using human cadaver skin with a Franz Diffusion Cell (see, Kristof (2017) Feasibility of transdermal delivery of Cyclosporine A using plasma discharges. Biointerphases. 12:02B402). Flux can be measured where the temperature of the Franz Diffusion Cell (and solutions inside the Franz Diffusion Cell) are held constant at about 17 degrees C., about 20 degrees C., about 23 degrees C. ("room temperature"), about 26 degrees C., about 30 degrees C., about 33 degrees C., about 37 degrees C. (mammalian body temperature), about 40 degrees C., and so on.

EXCLUSIONARY EMBODIMENTS

Excluding Chemicals

In exclusionary embodiments, the present disclosure can exclude any formulation, any composition, any dermal patch, or any method that comprises dihydromyricetin.

The present disclosure can exclude a composition, formulation, dermal patch, methods of use, methods of manufacture, that comprise one or more of the following: capsaicin, 2-arachidonylglycerol, curcumin, glycerylmonooleate, glycerylmonostearate, lecithin, acacia gum, xylitol, carboxymethylcellulose, a self-emulsifying agents, glycerol monostearate, glycerol monooleate, Cremophor RH40®, Cremophor EL®, hydroxypropyl cellulose, carbopol, poly(vinyl pyrrolidone), sodium carboxymethyl cellulose, hydroxyethyl cellulose, polycarbophil, pectin, chitosan, xanthan gum, locust bean gum, hydroxypropyl methylcellulose, poly(vinyl alcohol), poly(isoprene), poly(isobutylene). The present disclosure can also exclude one or more of, 23-lauryl ether, Aprotinin, Azone, Benzalkonium chloride, Cetylpyridinium chloride, Celyltrimethylammonium bromide, Cyclodextrin, Dextran sulfate, Lauric acid, Lauric acid/propylene glycol, Lysophosphatidylcholine, Menthol, Methoxysalicylate, Methyl oleate, Oleic acid, Phosphatidylcholine, Polyoxyethylene, Polysorbate 80, Sodium EDTA, Sodium glycocholate, Sodium glycodeoxycholate, Sodium lauryl sulfate, Sodium salicylate, Sodium taurocholate, Sodium taurodeoxycholate, Sulfoxides, and Alkyl glycosides. What can also be excluded is a formulation, composition, device, or method, that comprises pre-gelatinized starch, gelatinized starch, gelatinized corn starch, glycogelatin, alpha-tocopherol, glycogelatin, hemp oil, THC, CBD, gum acacia, sorbitol, xylitol, soy lecithin, a complex of two different gels (one with net negative charge and the other with net positive charge), and a compositions that comprise a solvent with a cosolvent.

What can be excluded is pharmaceutical compositions with 1-5% enhancer. What can be excluded is pharmaceutical compositions with 0.5-5% neutralizer, or with any amount of neutralizer What can be excluded is compositions with greater than 0%-5% by weight isopropyl myristate, or with any amount thereof. What can be excluded is pharmaceutical compositions with 0%-10% by weight carbopol, or with any amount of carbopol. What can be excluded is pharmaceutical compositions with about 10% ethanol, about 15%, about 20%, about 24%, about 30%, about 35%, about 40%, about 45%, about 50%, about 55%, about 60%, about 65%, about 70%, about 75%, about 80%, about 85%, about 90% ethanol.

For delivery of cannabinoids, for example, a system of solvent/cosolvent can be ethanol (solvent)/propylene glycol (cosolvent). Solvents can be anhydrous alcohol, ethanol, propanol, or isopropanol. Cosolvent can be propylene glycol or PEG. Ratio of solvent/cosolvent (by weight) can be about 5/95, about 10/90, about 15/85, about 20/80, about 25/75, about 30/70, about 35/65, about 40/60, about 45/55, about 50/50, about 55/45, about 60/40, about 65/35, about 70/30, about 75/25, about 80/20, about 85/15, about 90/10, about 95/5, and the like. In exclusionary embodiments, the present disclosure can exclude solvent/cosolvent compositions where the ratio is, 5/95, about 10/90, about 15/85, about 20/80, about 25/75, about 30/70, about 35/65, about 40/60, about 45/55, about 50/50, about 55/45, about 60/40, about 65/35, about 70/30, about 75/25, about 80/20, about 85/15, about 90/10, about 95/5, and the like.

Excluding Structures

The present disclosure can exclude an adhesive patch device, buccal patch device, sublingual drug delivery device, that has more than one reservoir. The patch device of the present disclosure can have only one reservoir, only two reservoirs, only three reservoirs, four reservoirs. The present disclosure can exclude microneedles, and can exclude a patch device that has microneedles. The present disclosure can exclude any adhesive patch device, buccal patch device, sublingual drug delivery device that comprises a bilaminate layer that comprises a trilaminate layer that comprises a tetralaminate layer. Also, the present disclosure can exclude a bilaminate layer, exclude a trilaminate layer, and exclude a tetralaminate layer.

What can be excluded is an adhesive polymer, or a device comprising an adhesive polymer, where the adhesive polymer has over 5 free hydroxyl groups per 100 atoms of the adhesive polymer.

Also, what can be excluded is an adhesive polymer, or a device comprising an adhesive polymer, where the adhesive polymer has over 10 free hydroxyl groups per 100 atoms of the adhesive polymer Moreover, what can be excluded is an adhesive polymer, or a device comprising an adhesive polymer, where the adhesive polymer has over 20 free hydroxyl groups per 100 atoms of the adhesive polymer, and so on.

In embodiments, what can be excluded is a monolith-type device where a backing is not in direct contact with a matrix of skin adhesive; where matrix of skin adhesive is not in direct contact with a releasable liner; where matrix does not comprise CBD; or all of the above.

Also, what can be excluded is a formulation, composition, device, lozenges, or sublingual pill that comprises one or more of sodium phosphate, potassium phosphate, guar gum, gum arabic, locust bean gum, xantfoan gum, carrageenan, carob gum, ghatti gum, pectin, tragacanth gum, acacia gum, mannitol, sorbitol, lactose, modified lactose, maltitol, mannitol, magnesium stearate, hydroxypropylmethylcellulose film, non-crystallizing sugar, or non-crystallizing sugar alcohol.

In embodiments, the present disclosure can exclude a reservoir-type device where backing does not directly contact reservoir; or where reservoir does not directly contact a hydrophilic porous membrane; or where hydrophilic porous membrane does not directly contact a release liner; or where reservoir does not contain all of: (1) a liquid carrier, (2) a gelling agent, and (3) CBD. Also, what can be excluded is a reservoir-type device that does not comprise all of the above.

In embodiments, what can be excluded is an adhesive polymer, or a device comprising an adhesive polymer, where the adhesive polymer reacts with amines. Also what can be excluded, is an adhesive polymer, or a device comprising an adhesive polymer, where the adhesive polymer has any free hydroxyl groups, where the adhesive polymer has over 1 free hydroxyl groups per 100 atoms of the adhesive polymer, where the adhesive polymer has over 5 free hydroxyl groups per 100 atoms of the adhesive polymer, where the adhesive polymer has over 10 free hydroxyl groups per 100 atoms of the adhesive polymer, where the adhesive polymer has over 20 free hydroxyl groups per 100 atoms of the adhesive polymer, and so on. For this exclusionary embodiments the skilled artisan understands that any polymer consists of a large number of atoms, for example, about five thousand atoms.

In embodiments, what can be excluded is a monolith-type device where a backing is not in direct contact with a matrix of skin adhesive; where matrix of skin adhesive is not in direct contact with a releasable liner; where matrix docs not comprise CBD; or all of the above.

What can also be excluded is a preparation, or a device comprising a preparation, where the preparation has over 1% gelling agent, over 2%, over 3%, over 4%, over 5%, over 6%, over 7%, over 8%, over 9%, over 10%, over 12%, over 14%, or over 16%, of gelling agent. Also, what can be excluded is a preparation, or a device comprising a preparation, where the preparation has under 1% gelling agent, under 2%, under 3%, under 4%, under 5%, under 6%, under 7%, under 8%, under 9%, under 10%, under 12%, under 14%, or under 16%, of gelling agent.

Excluding Enhancers

In exclusionary embodiments, the present disclosure can exclude any system, device, composition, reagent, or related method, that comprises one or more terpenes (e.g., d-limonene, 1,8-cineole, menthone, menthol, nerolidol, alpha-pinene, beta-carene, see, which is incorporated herein by reference in its entirety), 1-dodecyclazacycloheptane-2-one) (Azone®), oleic acid in propylene glycol, dodecyl-N,N-dimethylamino acetate (DDAA), dodecyl N,N-dimethylamino isopropionate (DDAIP), dimethylsulfoxide (DMSO), dimethylacetamide (DMA), ethanol, butanol, propanol, isopropanol, N-methyl pyrrolidone, lauryl alcohol, fatty acids (e.g., valeric, heptanoic, pelagonic, caproic, capric, lauric, myristic, stearic, caprylic, isovaleric), fatty acid esters, amides, cyclic amides such as Azone, surfactants (e.g., laurate, lauryl sulfate, cetyltrimethyl ammonium bromide, cetylpyridinium, tetradecyl-trimethylammonium), bile salts (cholate, taurocholic, deoxycholic), non-ionic detergents (e.g., Poloxamer, Brij, Span, Tween), urea, dimethylacetamide, dimethylformamide, a pyrrolidone compound, oxazolidinone, and the like. What can also be excluded is any system, device, composition, reagent, or related method that comprises an essential oil, such as peppermint oil, orange oil, lemon oil, and so on.

Excluding Cannabinoids

What can be excluded is any system, device, composition, reagent, and related methods that comprise tetrahydrocannabinolic acid (THCA), cannabidiolic acid (CBDA), and cannabigerolic acid (CBGA), or their decarboxylated their counterparts, tetrahydrocannabinol (THC), cannabidiol (CBD), and cannabigerol (CBG). What can be excluded is delta-9-tetrahydrocannabinol, delta-8-tetrahydrocannabinol, delta-9-tetrahydrocannabinol propyl analogue (THCV), cannabidiol (CBD), cannabidiol propyl analogues (CBDV), cannabichromene, cannabichromene propyl analogs, and cannabigerol.

In exclusionary embodiments, the present disclosure can exclude any system, device, composition, reagent, and related methods that comprise one or more of, cannabigerol; cannabichromene; cannabitriol; cannabidiol; cannabicyclolol; cannabielsoin; cannabinodiol; cannabinol; delta8- tetrahydrocannabinol; delta9-tetrahydrocannabinol; cannabichromanone; cannabicoumaronone; cannabicitnm; 10-oxo-delta6a10a-tetrahydrocannabinol; cannabiglendol; delta7-isotetrahydrocannabinol; CBLVA; CBV; CBEVA-B; CBCVA; delta-9-THCVA; CBDVA; CBGVA; divarinolic acid; quercetin; kaemferol; dihydrokaempferol; dihydroquercetin; cannflavin B; isovitexin; apigenin; naringenin; eriodictyol; luteolin; orientin; cytisosidr; vitexin; cammiprene; 3,4'-dihydroxy-5-methoxy bibenzyl; dihydroresveratrol; 3,4'dihydroxy-5,3'-dimethoxy-5'-isoprenyl; cannabistilbene 1; cannabistilbene 11a; cannabistilbene 11b; cannithrene 1; cannithrene 2; cannabispirone; iso-cannabispirone; cannabispirenon-A; cannabispirenone-B; cannabispiradienone; alpha-cannabispiranol; beta-cannabispiranol; acetyl-cannabispirol; 7-hydroxy-5-methoxyindan-1-spiro-cyclohexane; 5-hydroxy-7-methoxyindan-1-spiro cyclohexane; 5,7-dihydroxyindan-1-cyclohexane; cannabispiradienone; 3,4'-dihydroxy-5-methoxybibenzyl; canniprene; cannabispirone; cannithrene I; cannithrene 2; alpha-cannabispiranol; acetyl-cannabispirol; vomifoliol; dihydrovomifoliol; beta-ionone; dihydroactinidiolide; palustrine; palustridine; plus-cannabisativine; anhydrocannabisativine; dihydroperiphylline; cannabisin-A; cannabisin-B; cannabisin-C; cannabisin-D; grossamide; cannabisin-E; cannabisin-F; cannabisin-G; and so on (see, e.g., Flores-Sanchez and Verpoorte (2008) Secondary Metabolism in Cannabis. Phytochem. Rev. DOI 10.1007).

MORE EXCLUSIONARY EMBODIMENTS

In device embodiments, a device of the present/disclosure is substantially free of all cannabinoids that are not CBN. In composition embodiments, a composition of the present disclosure is substantially free of all cannabinoids that are not CBN.

In device embodiments, a device of the present disclosure is substantially free of one or more of tetrahydrocannabinol (THC), tetrahydrocannabinolic acid (THC-a), cannabinol (CBN), and cannabichromene (CBC). Also, a device of the present disclosure is substantially free each and every one of tetrahydrocannabinol (THC), tetrahydrocannabinols acid (THC-a), cannabinol (CBN), and cannabichromene (CBC). In composition embodiments, a composition of the present disclosure is substantially free of one or more of tetrahydrocannabinol (THC), tetrahydrocannabinolic acid (THC-a), cannabinol (CBN), and cannabichromene (CBC). Also, a composition of the present disclosure is substantially free each and every one of tetrahydrocannabinol (THC), tetrahydrocannabinolic acid (THC-a), cannabinol (CBN), and cannabichromene (CBC).

In one aspect, the term "substantially free" can mean that the quantity of one or more of THC, THC-a, CBN, and CBC, occurs at a molar quantity that is under 20%, under 15%, under 10%, under 5%, under 4%, under 2%, under 1%, under 0.5%, under 0.1%, under 0.05%, or under 0.01%, that of CBD. In another aspect, the term "substantially free" can mean that the quantity of each and every one of THC, THC-a, CBN, and CBC, occurs at a molar quantity that is under 20%, under 15%, under 10%, under 5%, under 4%, under 2%, under 1%, under 0.5%, under 0.1%, under 0.05%, or under 0.01%, that of CBD.

The following methods of measurement take into account the physical nature of a composition and the physical nature of the container or matrix that comprises a composition. In measuring a composition that is "substantially free," what can be measured is all compounds that are comprised by the composition, where the composition takes the form of an oil, a paste, a slurry, an adhesive, a powder, a solution, and the like, or that takes the form of a matrix, a reservoir, and impregnated fabric, a flask, a conduit, that holds, contains, absorbs, adsorbs, and the like, the oil, a paste, a slurry, an adhesive, a powder, a solution, and the like.

The present disclosure can exclude a system, device, composition, or related method, that comprises one or more of the following compounds: tackifier, adhesive, buprenorphine, clonidine, estradiol, fentanyl, granisetron, methylphenidate, nitroglycerin, oxybutynin, scopolamine, selegiline, testosterone, a vaccine, influenza virus vaccine, a mammalian hormone, a synthetic analogue of a mammalian hormone, a chemically modified mammalian hormone, lidocaine, estrogen, salicyclic acid, a contraceptive, rivastigmine, rotogotine, tulobuterol, adrenergic agonist, cholinesterase inhibitor, dopamine receptor agonist, oxybutynin, bupropion, varenicline, nicotine, antidepressant, smoking cessation drug, cholinsterase inhibitor, methylphenidate, buprenorphine, opioid analgesic agent, sumatriptan, antiviral drug, anti-retrovirus drug, mammalian steroid, chemical analogue of mammalian steroid, drug for attention-deficit hyperactivity disorder, and so on.

The present disclosure can exclude system, device, or related method that comprises a reservoir-type device where backing does not directly contact reservoir, or where reservoir does not directly contact a hydrophilic porous membrane; or where hydrophilic porous membrane does not directly contact a release liner; or where reservoir does not contain all of: (1) a liquid carrier, (2) a gelling agent, and (3) CBD. Also, what can be excluded is a reservoir-type device that does not comprise all of the above.

What can be excluded is an adhesive polymer, or a device comprising an adhesive polymer, where the adhesive polymer reacts with amines. Also what can be excluded, is an adhesive polymer, or a device comprising an adhesive polymer, where the adhesive polymer has any free hydroxyl groups, where the adhesive polymer has over 1 free hydroxyl groups per 100 atoms of the adhesive polymer, where the adhesive polymer has over 5 free hydroxyl groups per 100 atoms of the adhesive polymer, where the adhesive polymer has over 10 free hydroxyl groups per 100 atoms of the adhesive polymer, where the adhesive polymer has over 20 free hydroxyl groups per 100 atoms of the adhesive polymer, and so on. For this exclusionary embodiment, the skilled artisan understands that any polymer consists of a large number of atoms, for example, about five thousand atoms.

In embodiments, what can be excluded is a monolith-type device where a backing is not in direct contact with a matrix of skin adhesive; where matrix of skin adhesive is not in direct contact with a releasable liner; where matrix does not comprise CBD; or all of the above.

What can also be excluded is a preparation, or a device comprising a preparation, where the preparation has over 1% gelling agent, over 2%, over 3%, over 4%, over 5%, over 6%, over 7%, over 8%, over 9%, over 10%, over 12%, over 14%, or over 16%, of gelling agent. Also, what can be excluded is a preparation, or a device comprising a preparation, where the preparation, has under 1% gelling agent, under 2%, under 3%, under 4%, under 5%, under 6%, wider 7%, under 8%, under 9%, under 10%, under 12%, under 14%, or under 16%, of gelling agent.

What can also be excluded is a preparation, or a device comprising a preparation, where the preparation has over 1% penetration enhancer, over 2%, over 3%, over 4%, over 5%, over 6%, over 7%, over 8%, over 9%, over 10%, over 12%, over 14%, or over 16%, of penetration enhancer. Also, what can be excluded is a preparation, or a device comprising a preparation, where the preparation has under 1% penetration enhancer, under 2%, under 3%, under 4%, under 5%, under 6%, under 7%, under 8%, under 9%, under 10%, under 12%, under 14%, or under 16%, of penetration enhancer.

In other embodiments, what can be excluded is a preparation, a composition, a device comprising a preparation, a device comprising a composition, where said preparation or composition has a CBD (or THC, or combined weight of CBD and THC) content by weight of under 1%, under 2%, under 3%, under 4%, under 5%, under 6%, under 8%, under 10%, under 12%, under 14%, under 16%, under 18%, under 20%, under 25%, under 30%, under 35%, under 40%, under 45%, under 50%, under 55%, under 60%, under 65%, under 70%, under 75%, and so on. Also, what can be excluded is a preparation, a composition, a device comprising a preparation, a device comprising a composition, where said preparation or composition has a CBD (or THC, or combined weight of CBD and THC) content by weight that is greater than 5%, greater than 6%, greater than 7%, greater than 8%, greater than 10%, greater than 12%, greater than 14%, greater than 16%, greater than 18%, greater than 20%, greater than 25%, greater than 30%, greater than 35%, greater than 40%, greater than 45%, greater than 50%, greater than 55%, greater than 60%, greater than 65%, greater than 70%, and so on. In embodiments, what can be excluded is a preparation, a composition, a device comprising a preparation, or a device comprising a composition, where the percent by weight is defined by one or more of the above "under" or "greater than" parameters. "Composition" can refer to, for example, matrix of a skin adhesive, or to fluid in hydrophilic porous membrane, and so on. Alternatively, the present disclosure can comprise one or more of the above compositions, as set forth by "under" parameters or "greater than" parameters.

Moreover, in embodiments what can be excluded is any device that does not include an occlusive system polymer film that does not include a polyethylene occlusive polymer film that does not include a PET occlusive polymer film that does not include an occlusive polymer film made of both polyethylene and PET. Also, what can be excluded is a device that has an overlay patch, and a device that does not comprise an overlay patch.

In embodiments, polar organic liquid can comprise, or can exclude, one or more of methanol, ethanol, propanol, isopropanol, butanol, pentanol, acetic acid, propionic acid, butyric acid, valeric acid, caproic acid, caprylic acid, capric acid, lauric acid, myristic acid palmitic acid, stearic acid, palmitoleic acid, oleic acid, linoleic acid, linolenic acid, linear alkanes of 5, 6, 7, 8, 9, 10, 11, 12, 13, 14, 15, 16, 17, 18, 19, 20, 21, 22, 23, 24, or more carbons, branched chain alkanes with a backbone of 5, 6, 7, 8, 9, 10, 11, 12, 13, 14, 15, 16, 17, 18, 19, 20, 21, 22, 23, 24, or more carbons, linear alkenes (olefins) of 5, 6, 7, 8, 9, 10, 11, 12, 13, 14, 15, 16, 17, 18, 19, 20, 21, 22, 23, 24, or more carbons, branched, chain alkenes (olefins) with a backbone of 5, 6, 7, 8, 9, 10, 11, 12, 13, 14, 15, 16, 17, 18, 19, 20, 21, 22, 23, 24, or more carbons, and so on. Alternatively, the present disclosure can comprise one or more of the above polar organic liquids.

EXAMPLES

Example One

Stress Less Formulation

Active ingredients: Hemp cannabidiol (1.5 mg); menthol (6 mg), camphor (1.5 mg). Inactive ingredients: synthetic rubber polymer, polyester terephthalate, polyethylene.

Active ingredients can be combined and used in a reservoir formulation, where the reservoir formulation can include one or more of the inactive ingredients. Also, active ingredients can be combined and used in a monolithic patch formulation, where the monolithic patch formulation can include one or more of the inactive ingredients.

Stress Less Formulation optionally includes dihydromyricetin.

Example Two

PMS Formulation

The disclosure provides formulations and dermal patches for use in treating, preventing, or mitigating premenstrual syndrome (PMS). Active ingredients: Hemp cannabidiol (15 mg); soy isoflavones extract (5 mg), black cohosh extract (5 mg), menthol (6 mg), camphor (1.5 mg). Inactive ingredients: synthetic rubber polymer, polyester terephthalate, polyethylene. Cohosh extract is available from Sigma-Aldrich, St. Louis, Mo.

Active ingredients can be combined and used in a reservoir formulation, where the reservoir formulation can include one or more of the inactive ingredients. Also, active ingredients can be combined and used in a monolithic patch formulation, where the monolithic patch formulation can include one or more of the inactive ingredients.

PMS Formulation optionally includes dihydroxymyricetin.

Example Three

Hangover Healer Formulation

Active ingredients: Hemp cannabidiol (15 mg); dihydromyricetin (8 mg). Inactive ingredients: synthetic rubber polymer, polyester terephthalate, polyethylene.

Active ingredients can be combined and used in a reservoir formulation, where the reservoir formulation can include one or more of the inactive ingredients. Also, active ingredients can be combined and used in a monolithic patch formulation, where the monolithic patch formulation can include one or more of the inactive ingredients.

Example Four

Nite Formulation

Active ingredients: hemp cannabidiol (15 mg); melatonin (6 mg). Inactive ingredients: synthetic rubber polymer, polyester terephthalate, polyethylene.

Active ingredients can be combined and used in a reservoir formulation, where the reservoir formulation can include one or more of the inactive ingredients. Also, active ingredients can be combined and used in a monolithic patch formulation, where the monolithic patch formulation can include one or more of the inactive ingredients.

Nite Nite Formulation optionally includes dihydromyricetin.

Example Five

Ratio of Formulation Components

Ratio of cannabidiol (CBD)/dihydromyricetin (wt./wt.) in a formulation can be (or can be greater than, or can be lesser than), for example, about 1/0.01, about 1/0.02, about 1/0.04, about 1/0.06, about 1/0.08, about 1/0.10, about 1/0.2, about 1/0.4, about 1/0.6, about 1/0.8, about 1/1.0, about 1/2, about 1/4, about 1/8, about 1/10, about 1/15, about 1/20, about 1/25, about 1/30, about 1/35, about 1/40, about 1/45, about 1/50, about 1/55, about 1/60, about 1/65, about 1/70, about 1/75, about 1/80, about 1/85, about 1/90, about 1/95, about 1/100, and the like.

The ratio of the sum of all cannabinoids/dihydromyricetin (wt./wt.) can be (or can be greater than, or can be lesser than), for example, about 1/0.01, about 1/0.02, about 1/0.04, about 1/0.06, about 1/0.08, about 1/0.10, about 1/0.2, about 1/0.4, about 1/0.6, about 1/0.8, about 1/1.0, about 1/2, about 1/4, about 1/8, about 1/10, about 1/15, about 1/20, about 1/25, about 1/30, about 1/35, about 1/40, about 1/45, about 1/50, about 1/55, about 1/60, about 1/65, about 1/70, about 1/75, about 1/80, about 1/85, about 1/90, about 1/95, about 1/100, and the like.

Example Six

Dihydromyrecitin Enhances Cannabinoid Absorption Into Skin

The inventors discovered that dihydromyrecitin, when present in a dermal patch formulation that includes cannabidiol (CBD), increases absorption of the CBD into human skin, as demonstrated by the human cadaver skin using Franz Diffusion Cell method. The inventors discovered that the dihydromyrecitin increased flux through skin by a factor of three-fold.

In view of the advantageous data showing increased flux, the inventors provide formulations, compositions, adhesive compositions, and the like that contain dihydromyrecitin in combination with one or more cannabinoids. Cannabinoids can be one or more of cannabidiol (CBD), cannabinol (CBN), tetrahydrocannabinolic acid (THCa), delta-9-THC, delta-8-THC, and so on.

Example Seven

FIG. 1 and FIG. 2

For each figure, the number of hours that flux was allowed to occur was twentyfour hours (24 hours). The data for each figure used a monolithic patch. Composition of the patch: PIB adhesive with 15% of CBD or 8% THC. Patch construction was adhesive layer attached to a backing polyethylene foam film. No additional overlays were used. Experiments were done using Franz Diffusion Cells using human cadaver skin.

FIG. 1. In vitro transdermal flux of THC through human cadaver epidermis from patches containing 8% THC and either, no enhancer (first bar) where result is about 90 micrograms/cm$^2$, 3% oleic acid (second bar) where result is about 110 micrograms/cm$^2$, or 0.5% dihydromyricetin where result is about 145 micrograms/cm$^2$. The values show cumulative flux. The stimulation with 5% dihydromyricetin (third histogram bar) is about 61% stimulation (this means that, with stimulation, the cumulative flux is 61% greater than without any dihydromyricetin).

FIG. 2. In vitro transdermal flux of CBD through human cadaver epidermis from patches containing 15% CBD and dihydromyricetin as a penetration enhancer, with either 0% dihydromyricetin (first bar) where result is about 155 micrograms/cm$^2$, 3% dihydromyricetin (second bar) where result is about 195 micrograms/cm$^2$, or 5% dihydromyricetin (third bar) where result is about 230 micrograms/cm$^2$. The values show cumulative flux. The stimulation with 3% dihydromyricetin is about 25% stimulation (this means that, with stimulation, the cumulative flux is 25% greater than without any dihydromyricetin). The stimulation with 5% dihydromyricetin is about 48% stimulation.

The present disclosure provides a dermal patch that contains CBD and dihydromyricetin, where the dihydromyricetin stimulates cumulative flux to achieve an amount that is at least The present invention is not to be limited by compositions, reagents, methods, diagnostics, laboratory data, and the like, of the present disclosure. Also, the present invention is not be limited by any preferred embodiments that are disclosed herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination, with other members of the group or other elements found herein. It is anticipated that one or more members of a group may be included in, or deleted from, a group for reasons of con venience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

As one skilled in the art would recognize as necessary or best-suited for performance of the methods of the invention, a computer system or machines of the invention include one or more processors (e.g., a central processing unit (CPU) a graphics processing unit (GPU) or both), a main memory and a static memory, which communicate with each other via a bus.

A processor may be provided by one or more processors including, for example, one or more of a single core or multi-core processor (e.g., AMD Phenom II X2. Intel Core Duo, AMD Phenom II X4, Intel Core i5, Intel Core i& Extreme Edition 980X, or Intel Xeon E7-2820).

An I/O mechanism may include a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), an accelerometer, a microphone, a cellular radio frequency antenna, and a network interface device (e.g., a network interface card (NIC), Wi-Fi card, cellular modem, data jack, Ethernet port, modem jack, HDMI port, mini-HDMI port, USB port), touchscreen (e.g., CRT, LCD, LED, AMOLED, Super AMOLED), pointing device, trackpad, light (e.g., LED), light/image projection device, or a combination thereof.

Memory according to the invention refers to a non-transitory memory which is provided by one or more tangible devices which preferably include one or more machine-readable medium on which is stored one or more sets of instructions (e.g., software) embodying any one or more of the methodologies or functions described herein. The software may also reside, completely or at least partially, within the main memory, processor, or both during execution thereof by a computer within system, the main memory and the processor also constituting machine-readable media. The software may further be transmitted or received over a network via the network interface device.

While the machine-readable medium can in an exemplary embodiment be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. Memory may be, for example, one or more of a hard disk drive, solid state drive (SSD), an optical disc, flash memory, zip disk, tape drive, "cloud" storage location, or a combination thereof. In certain embodiments, a device of the invention includes a tangible, non-transitory computer readable medium for memory. Exemplary devices for use as memory include semiconductor memory devices, (e.g., EPROM, EEPROM, solid state drive (SSD), and flash memory devices e.g., SD, micro SD, SDXC, SDIO, SDHC cards); magnetic disks, (e.g., internal hard disks or removable disks); and optical disks (e.g., CD and DVD disks).

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A monolithic patch that comprises polyisobutylene (PIB) adhesive, with the penetration enhancer dihydromyricetin, and with 15% of cannabidiol (CBD), wherein the construction comprises an adhesive layer attached to a backing, and wherein the monolithic patch is capable of delivering CBD at a net flux of at least 195 micrograms CBD per square centimeter of skin over a period of 24 hours, as compared to a control net flux of about 155 micrograms CBD per square centimeter of skin over a period of 24 hours for a control monolithic patch that does not contain any dihydromyricetin wherein the dihydromyricetin concentration is about 0.5% about 1.0%, about 2.0%, about 3.0%, about 4.0%, or about 5.0% dihydromyricetin.

2. The monolithic patch of claim 1, wherein the backing comprises polyethylene foam film.

3. The monolithic patch of claim 2 that does not contain any type of overlay that is in addition to the polyethylene foam film.

4. The monolithic patch of claim 1, wherein the cannabinoid flux is measured or is measurable with a Franz diffusion cell and human cadaver skin.

5. The monolithic patch of claim 1 that does not comprise any penetration enhancer aside from dihydromyricetin.

6. The monolithic patch of claim 1 that does not comprise any combination of azone, oleic acid, a terpene, and ethanol.

7. The monolithic patch of claim 1 that does not comprise one or more of azone, oleic acid, a terpene, and ethanol.

8. The monolithic patch of claim 1, wherein the only cannabinoid present is CBD.

* * * * *